(12) United States Patent
Alford et al.

(10) Patent No.: US 9,060,507 B2
(45) Date of Patent: Jun. 23, 2015

(54) PERFUSION SOLUTION

(75) Inventors: Marlin Alford, Kaufman, TX (US); Robert Dowben, Providence, RI (US); Franklin Rosenfeldt, North Balwyn (AU)

(73) Assignee: Perfusion Fluid Technologies Inc, Redlands, CA (US)

( * ) Notice: Subject to any disclaimer, the term of this patent is extended or adjusted under 35 U.S.C. 154(b) by 0 days.

(21) Appl. No.: 13/818,670

(22) PCT Filed: Sep. 1, 2011

(86) PCT No.: PCT/AU2011/001121
§ 371 (c)(1),
(2), (4) Date: Feb. 23, 2013

(87) PCT Pub. No.: WO2012/027787
PCT Pub. Date: Mar. 8, 2012

(65) Prior Publication Data
US 2013/0203041 A1   Aug. 8, 2013

Related U.S. Application Data

(60) Provisional application No. 61/379,207, filed on Sep. 1, 2010, provisional application No. 61/474,722, filed on Apr. 12, 2011.

(51) Int. Cl.
*A01N 1/02* (2006.01)
(52) U.S. Cl.
CPC .................................. *A01N 1/0226* (2013.01)
(58) Field of Classification Search
USPC ......................................................... 435/1.2
See application file for complete search history.

(56) References Cited

U.S. PATENT DOCUMENTS

| | | | |
|---|---|---|---|
| 5,565,317 A * | 10/1996 | Dohi et al. | ...................... 435/1.2 |
| 5,965,433 A | 10/1999 | Gardetto et al. | |
| 6,046,046 A | 4/2000 | Hassanein | |
| 6,677,150 B2 | 1/2004 | Alford et al. | |
| 6,977,140 B1 | 12/2005 | Owen et al. | |
| 7,897,327 B2 | 3/2011 | Millis et al. | |
| 2006/0292544 A1 | 12/2006 | Hassanein et al. | |
| 2007/0190636 A1 | 8/2007 | Hassanein et al. | |
| 2007/0275364 A1 | 11/2007 | Hassanein et al. | |

FOREIGN PATENT DOCUMENTS

| | | | |
|---|---|---|---|
| WO | PCT/NL2005/050036 | 5/2006 | |
| WO | WO2006052133 | * 5/2006 | |
| WO | PCT/US2006/016163 | 11/2006 | |
| WO | WO2006118990 | * 11/2006 | ............... C12M 3/00 |
| WO | PCT/US2008/061454 | 12/2008 | |
| WO | PCT/SE2010/000227 | 3/2011 | |

OTHER PUBLICATIONS

Shimada et al. The effect of continuous perfusion with St. Thomas' Hospital cardioplegic solution containing glucose, insulin and L-aspartate on functional recovery after myocardial preservation in the rat. Nihon Kyobu Geka Gakkai Zasshi. 1996;44(9):1742-8.*

* cited by examiner

*Primary Examiner* — Ruth Davis
*Assistant Examiner* — Lynn Y Fan
(74) *Attorney, Agent, or Firm* — Law Offices of Ken Dallara; Ken Dallara

(57) ABSTRACT

The invention provides a perfusion stock composition, for preserving a donor organ for transplantation, comprising: a source of 60 to 100 mM $Na^+$; a source of 10 to 20 mM $K^+$; a source of 5 to 10 mM $Mg^{2+}$; a source of 0.25 to 0.75 mM $Ca^{2+}$; 10 to 40 mM Tris(hydroxymethyl)aminomethane hydrochloride (Tris or THAM), 4-(2-hydroxyethyl)-1-piperazineethanesulfonic acid (HEPES), 3-(N-morpholino)propanesulfonic acid (MOPS), 2-(N-morpholino)ethanesulfonic acid (MES), N,/N-bis-(2-hydroxyethyl)-2-aminoethansulfonic acid (BES), or N/-tris(hydroxymethyl)methyl-2-aminoethanesulfonic acid (TES); a source of 10 to 30 mM $HCO_3^-$; 1 to 30 mM glucose; 1 to 20 U/L insulin; 1 to 10 mM fructose diphosphate or a salt thereof; 1 to 40 mM aspartate or glutamate; 1 to 10 mM adenosine, cAMP or cGMP; 1 to 10 mM reduced glutathione; and 30 to 100 mM lactobionate or mannitol; and optionally a diluent. The invention also provides a perfusion composition, a kit, a method, and a perfusion apparatus, each related to the perfusion stock composition.

2 Claims, 14 Drawing Sheets

PERFUSION SOLUTION

FIELD

The invention relates to a perfusion composition and a method for preserving a donor organ for transplantation. The invention also relates to a perfusion stock solution for preparing the perfusion composition, a kit comprising the perfusion stock composition or perfusion composition, and a perfusion apparatus for perfusing the donor organ with the perfusion composition.

BACKGROUND

It is to be understood that, if any prior art publication is referred to herein, such reference does not constitute an admission that the publication forms a part of the common general knowledge in the art, in Australia or any other country.

The surgical transplantation of organs has been successfully performed since 1960 owing to the improvement of surgical techniques, the introduction of by-pass circulation and the development of drugs that suppress immune rejection of the donor organ. Organ viability or survival is a critical link in the chain of donation, transportation and transplantation and has a significant effect on post-transplant organ function and organ survival.

There is a shortage of organ donors around the world. Currently, organs for transplantation come from a very limited number of brain dead donors in whom the heart and the circulation are still functioning. The donation after cardiac death (DCD) donor (also known as a marginal or non-heart beating donor) is another type of donor pronounced dead based on cardiopulmonary arrest. DCD donation has expanded clinical transplantation of the kidney, liver and lung. Because the heart is more susceptible to warm ischemia than any other transplantable organ, it presents a considerably greater challenge for DCD donation.

One method to prolong organ viability involves warm perfusion of the organ, maintaining physiological pressure and flow parameters. Such methods essentially rely on a heart lung machine to perfuse blood. A vast quantity of blood of the correct blood type is required to avoid any blood incompatibility reactions with either the donor heart or with the recipient. The blood must be anticoagulated. The blood type antigens are located on the red cell membranes, so that using purified hemoglobin instead of whole blood eliminates any blood incompatibility reactions, but exposes the recipient to the complications of hemoglobin transfusions. Alternatively, plasma and chemical solutions have been used for warm perfusion. However, the devices required for warm perfusion are bulky, awkward, heavy, difficult to transport, and expensive.

It has long been known that organs will survive ex vivo for a longer time if they are cooled to 4° C., because metabolism is greatly reduced, lowering the requirements for nutrients and oxygen, and the production of lactic acid and other toxic end products of metabolism are also greatly reduced. Accordingly, passive preservation and active perfusion of donor organs have each been performed at reduced temperatures, commonly 4° C.

Cardiac preservation has changed relatively little in recent years. Clinically, the most widely used form of preservation is hypothermic preservation, which is based on the reduction of cellular metabolism by hypothermia. Just before the donor heart is harvested, a cardioplegic solution at 4° C. is injected into the donor's circulation to stop the heart beating and minimize energy consumption. The donor heart is promptly harvested under sterile conditions, then quickly washed with ice cold iso-osmotic saline solution. The heart is then put into a plastic bag containing a preservation solution (a buffered salt solution containing nutrients) and kept on ice until transplantation. The solution is not oxygenated and is not perfused through the organ blood vessels. Advantages of hypothermic preservation include universal availability and ease of transport. However, 4 hours is the generally accepted limit of cold ischemia. Furthermore, hypothermic preservation has not been successful in transplantation from DCD hearts, thus restricting the pool of potential organs for transplantation.

Alternatively, hypothermic perfusion, developed in 1967, relies on perfusion through the vascular bed of the organ with a buffered salt solution containing nutrients. Ex vivo survival of an isolated organ can be extended further if the perfusion solution is oxygenated. The perfusion fluid continuously replenishes the oxygen and nutrients available to the organ, removes lactic acid and other toxic metabolites, and maintains ion-pump activity and metabolism, including synthesis of adenosine triphosphate (ATP) and other molecules. The buffer maintains the physiological pH and tonic strength of the organ. Cold perfusion methods have increased the viability of transplanted organs for a longer period of time but are generally limited to 6 to 8 hour period of ischemia.

Several hypothermic preservation solutions are available. The Collins preservation solution contains high concentrations of potassium, magnesium, phosphate, sulphate, and glucose. The high level of glucose acts as an effective osmotic agent which suppresses cell swelling. Magnesium acts as a membrane stabilizer, but in the presence of phosphate, magnesium phosphate formed a precipitate. Euro-Collins solution is a modification of the original Collins solution and contains high concentrations of potassium, phosphate, and glucose, but lacks magnesium.

The Ross-Marshall preservation solutions were developed as alternatives to the Collins solutions. Their electrolytic compositions are similar except that citrate replaces phosphate, and mannitol replaces glucose. The citrate acts as a buffer and chelates with magnesium to form an impermeable molecule that helps stabilize the extracellular environment.

The University of Wisconsin (UW) preservation solution was developed for liver, kidney, and pancreas preservation. It has been considered the standard for renal and hepatic preservation, effectively extending the ischemic time for kidneys and livers and allowing them to be transported considerable distances to waiting recipients.

The Bretschneider preservation solution includes histidine, mannitol, tryptophan and alpha-ketoglutaric acid. It also contains low concentrations of sodium, potassium, and magnesium. Histidine serves as a buffer, and tryptophan, histidine, and mannitol act as oxygen free-radical scavengers.

Celsior® is a recently developed extracellular-type, low-viscosity preservation solution that couples the impermeant, inert osmotic carrier from UW solution and the strong buffer from Bretschneider solution. The reduced glutathione in Celsior® solution is used as an antioxidant removing dangerous free-radicals. The solution was specifically designed for heart transplantation.

Some preservation solutions have introduced compounds which are believed to increase the viability of the organ during and after transport, for example neuregulin or taxol.

Importantly, preservation solutions are not designed for perfusion. Nevertheless, many preservation solutions have been used to perfuse hearts. With the exception of Celsior®, they will not work as perfusion solutions, and Celsior® does not work as well as specifically tailored perfusion solutions.

In general, preservation solutions are viscous and require machine perfusion. Perfusion using preservation solutions is often incomplete, not reaching the distal vessels in the apex of the heart. For example, the Wisconsin solution is so viscous that it will not flow through the capillary bed. Perfusion with preservation solutions has resulted in a little prolongation of heart viability. Solutions with an intracellular electrolyte profile are toxic as perfusion solutions. A number of reports describe injecting solution into the inferior vena cava flushing out the right atrium and right ventricle, and injecting solution into the pulmonary vein flushing out the left atrium and left ventricle. This is not perfusion, although it is sometimes called that.

Therefore, there is a need for a perfusion solution that improves the preservation and viability of donor organs, particularly hearts, particularly DCD hearts, for transplantation.

SUMMARY

A first aspect provides a perfusion stock composition, for preserving a donor organ for transplantation, comprising:
(a) a source of 60 to 100 mM $Na^+$;
(b) a source of 10 to 20 mM $K^+$;
(c) a source of 5 to 10 mM $Mg^{2+}$;
(d) a source of 0.25 to 0.75 mM $Ca^{2+}$;
(e) 10 to 40 mM Tris(hydroxymethyl)aminomethane hydrochloride (Tris or THAM), 4-(2-hydroxyethyl)-1-piperazineethanesulfonic acid (HEPES), 3-(N-morpholino)propanesulfonic acid (MOPS), 2-(N-morpholino)ethanesulfonic acid (MES), N,N-bis-(2-hydroxyethyl)-2-aminoethansulfonic acid (BES), or N-tris(hydroxymethyl)methyl-2-aminoethanesulfonic acid (TES);
(f) a source of 10 to 30 mM $HCO_3^-$;
(g) 1 to 30 mM glucose;
(h) 1 to 20 U/L insulin;
(i) 1 to 10 mM fructose diphosphate or a salt thereof;
(j) 1 to 40 mM aspartate or glutamate;
(k) 1 to 10 mM adenosine, cAMP or cGMP;
(l) 1 to 10 mM reduced glutathione; and
(m) 30 to 100 mM lactobionate or mannitol; and optionally
(n) a diluent.

A second aspect provides a perfusion composition comprising the perfusion stock composition of the first aspect and a diluent, wherein the perfusion composition has pH of 7.2 to 7.4 and osmolarity of 280 to 380 mOsm/L.

A third aspect provides a kit, for preparing a perfusion composition for preserving a donor organ for transplantation, comprising a perfusion stock composition comprising:
(a) a source of 60 to 100 mM $Na^+$;
(b) a source of 10 to 20 mM $K^+$;
(c) a source of 5 to 10 mM $Mg^{2+}$;
(d) a source of 0.25 to 0.75 mM $Ca^{2+}$;
(e) 10 to 40 mM Tris, HEPES, MOPS, MEP, BES or TES;
(f) a source of 10 to 30 mM $HCO_3^-$;
(g) 1 to 30 mM glucose;
(h) 1 to 40 mM aspartate or glutamate;
(i) 1 to 10 mM adenosine, cAMP or cGMP;
(j) 30 to 100 mM lactobionate or mannitol;
(k) 1 to 20 U/L insulin;
(l) 1 to 10 mM fructose diphosphate or a salt thereof; and
(m) 1 to 10 mM reduced glutathione; and optionally
(n) a diluent,
wherein optionally (a) to (j) are separated from (k) to (m) and optionally (n), wherein in use (a) to (m) and optionally (n) are combined to prepare the perfusion composition, wherein the perfusion composition has pH of 7.2 to 7.4 and has osmolarity of 280 to 380 mOsm/L.

A fourth aspect provides a method of preserving a donor organ for transplantation, the method comprising perfusing at 5 to 10° C. the donor organ with a perfusion composition comprising:
(a) a source of 60 to 100 mM $Na^+$;
(b) a source of 10 to 20 mM $K^+$;
(c) a source of 5 to 10 mM $Mg^{2+}$;
(d) a source of 0.25 to 0.75 mM $Ca^{2+}$;
(e) 10 to 40 mM Tris, HEPES, MOPS, MEP, BES or TES;
(f) a source of 10 to 30 mM $HCO_3^-$;
(g) 1 to 30 mM glucose;
(h) 1 to 20 U/L insulin;
(i) 1 to 10 mM fructose diphosphate or a salt thereof;
(j) 1 to 40 mM aspartate or glutamate;
(k) 1 to 10 mM adenosine, cAMP or cGMP;
(l) 1 to 10 mM reduced glutathione;
(m) 30 to 100 mM lactobionate or mannitol; and
(n) 50 to 100% saturation $O_2$,
wherein the perfusion composition has pH of 7.2 to 7.4, osmolarity of 280 to 380 mOsm/L.

According to a further aspect of the present invention there is provided a perfusion apparatus comprising a temperature controlled enclosure containing a perfusion solution reservoir adapted to be coupled to the aortic root of a heart via an adjustable valve, and means to suspend the heart from the aortic root whereby the perfusion solution is gravity fed through the heart for collection.

Although organ transplantation has been undertaken for 50 years, there is no known perfusion composition or method of preserving a donor organ that will guarantee organ viability in the organ recipient. Incremental improvements have been made under specific circumstances, for example hypothermic preservation, hypothermic perfusion preservation, and hypothermic crystalloid perfusion. Numerous compositions, e.g. solutions, have been developed for use in such preservation techniques. Nevertheless, a universal or near universal perfusion composition for preserving donor organs for transplantation is not known. Consequently, there is s long felt need for such a universal or near universal perfusion composition that can improve donor organ viability.

The inventors have now developed such a universal or near universal perfusion composition with the following advantages:

1. Prolongation of preservation of the donor organ, particularly the DCD donor heart, beyond the current 4 hour limit of standard preservation;
2. Facilitation of aerobic metabolism of the donor organ, particularly the DCD donor heart, during preservation;
3. Provision of superior functional and metabolic recovery of the donor organ, particularly the DCD donor heart, compared to standard preservation (standard cardioplegia and cold storage);
4. Allowance of recovery of the donor organ, particularly the DCD donor heart, sufficient for transplantation;
5. Promotion of resuscitation of the damaged donor organ, particularly the DCD donor heart, during and after transplantation; and
6. Simplicity and practicality for clinical application.

In other words, the inventors have developed a perfusion composition and a method for preserving donor organs for transplantation that not only prolongs the preservation period and hence the viability of the organ, but also promotes recovery and resuscitation of the donor organ in the organ recipient.

Although the inventors conclude that the perfusion composition and method is suitable for heart, kidney, liver, lung and heart transplantation, the inventors have demonstrated that the perfusion composition and method is particularly suited to DCD donor organ transplantation and particularly heart transplantation.

DETAILED DESCRIPTION

Perfusion Preservation

Figure 1:
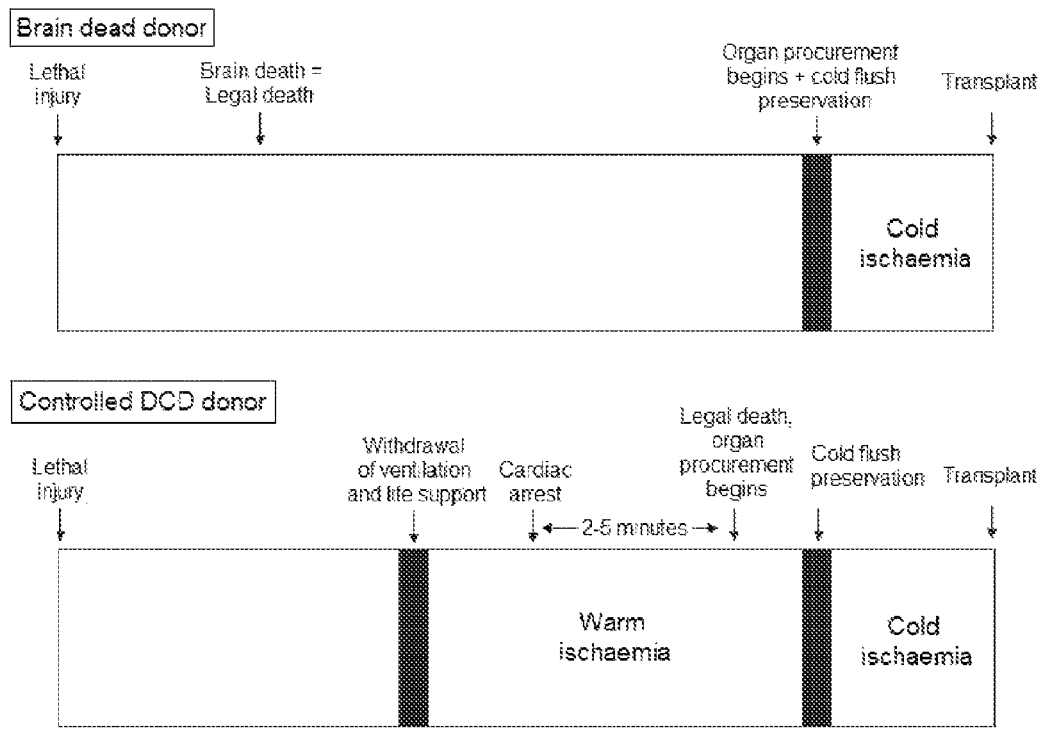
FIG. 1 is a diagrammatic comparison of the brain dead and controlled donation after cardiac death (DCD) donor.

The present invention relates to a perfusion composition, which, when perfused through an ex vivo organ, will sustain the critical chemical balances necessary to minimize cellular and reperfusion damage. Thus, the invention also relates to a method of preserving a donor organ for transplantation. This invention accounts for the potassium/sodium balance in cells and the elimination of harmful free radicals during ischemia. Though this perfusion composition is exemplified as a cardiac perfusion composition, the composition may be used to perfuse other organs, such as kidney, liver, lung and pancreas.

As used herein, "preserve", "preservation" and similar terms refer to maintenance of viability of a donor organ from harvest to reanimation in the organ recipient so that the donor organ performs comparably in the recipient as it did in the donor prior to donation.

As used herein, a "preservation" composition is a composition designed to passively preserve a donor organ in the absence of perfusion. In contrast, as used herein, a "perfusion" composition is a composition designed to actively preserve a donor organ by perfusion.

As an organ is harvested, the organ immediately begins to degrade due to ischemia and these organs are then subject to reperfusion injury when the transplanted organ is introduced to its new host. This damage to tissue can continue when blood supply returns to the tissue after a period of ischemia, in particular the oxygen that is carried in the blood. Reintroduction of oxygen causes a greater production of damaging free radicals as well as allowing, via removal of the extracellular acidotic conditions, influx of calcium and thus calcium overloading. Such radicals can attack cell membrane lipids, proteins, and glycosaminoglycans, causing further damage. The absence of oxygen and nutrients from blood also creates a condition in which the reperfusion results in inflammation and oxidative damage through the induction of oxidative stress rather than restoration of normal function. Another issue in maintaining cell life outside the body during a period of ischemia, is the prevention of lethal changes in cellular hydration. It is critical that the perfusion composition maintain as many nutrients that the organ cells require to maintain cellular integrity and that free radicals, toxins and wastes are removed from the cells as they would in a normally functioning organ.

Cold, or hypothermic, perfusion decreases the rate of cellular collapse and destruction due to the decrease in metabolic activity but metabolism is not completely suppressed. Cooling from 37° C. to 10° C. reduces cellular metabolism around 12-fold, whereas further cooling to 2 to 4° C. reduces cellular metabolism between 20 and 40-fold. In one embodiment, the perfusion composition of the invention is used to perfuse organs between 2 and 10° C. In another embodiment, the perfusion composition may be used to perfuse organs at 2, 3, 4, 5, 6, 7, 8, 9, 10, 11, 12, 13, 14, 15, 16, 17, 18, 19, 20° C., or any range there between. This decreases metabolic activity and slows enzymatic degradation of cellular components and also decreases the organ's demand for oxygen and organic substances that the organ requires for normal activity, and thus also decreases the waste by-products of that metabolic activity including toxic acids, wastes and production of free-radicals. Although metabolism and utilization of cellular energy stores are slowed, ATP and adenosine diphosphate (ADP), the major sources of cellular metabolic energy, are also gradually depleted during hypothermia. Hypothermia can also cause a phase transition of lipids and result in reducedmembrane stability. In addition, it drastically alters the function of membrane bound enzymes. Hypothermia-induced structural changes in the membrane increase permeability, which contributes to cell swelling.

Perfusion at 4 to 8° C. balances the need to reduce overall metabolism, but to maintain basal aerobic metabolism in preference to basal anaerobic metabolism.

A principal goal during cold perfusion of an ischemic heart is to maintain the integrity of the cardiac cell membrane, and the integrity of the cardiac cell membrane potential. The cardiac cell normally has a high concentration of potassium and a low concentration of sodium, while the extracellular fluid has a low potassium concentration and high sodium concentration. The intracellular cardiac ion concentrations are maintained by pumping sodium ions out of the cell by an energetically driven process. When the heart is cooled, energy production by oxidative phosphorylation stops, and sodium ions are no longer pumped out. The intracellular sodium concentration then increases. The sodium overload produced is accompanied by an abnormally high calcium influx that causes muscle cell injury and death by several different mechanisms. Under these conditions, a switch from aerobic to anaerobic glycolysis is accomplished but the production of lactic acid also increases.

Donation After Cardiac Death (DCD)

Currently, almost all donor hearts are obtained from a limited number of brain dead donors. The criteria for brain death were introduced in 1968 and today are accepted throughout the world. Brain death describes the irreversible cessation of function of the entire brain, including the brain-stem. The diagnosis of brain death is made clinically, although other investigations such as computed tomography (CT), cerebral angiography and electroencephalography (EEG) can assist the process.

Until recently, most transplanted organs have come from standard criteria donors. These are brain dead donors, also called heart-beating donors (HBDs), who meet strict medical criteria for donation. Standard criteria donors are regarded as the 'ideal' donor due to their young age, favourable medical condition and location within the hospital intensive care unit (ICU) which allows timely organ procurement, the immediate initiation of preservation techniques and reduction of ischemic time. In an attempt to increase transplantation, some transplant units have begun utilising organs not considered ideal by standard criteria (e.g. organs from older patients), referred to as marginal donors or expanded criteria donors.

Another potential source of donor organs is the "donation after cardiac death" or "DCD" donor. In DCD, two criteria must be fulfilled to diagnose the donor as dead. The first is cessation of cardiopulmonary function i.e. asystole, apnoea and absence of response to stimuli. The second is that the cessation of function is irreversible. At the Alfred Hospital, Melbourne, Australia, the DCD donor is declared dead 5 minutes after the onset of cardiac arrest (asystole), which is defined as the lack of a palpable pulse and/or the absence of electrical activity on electrocardiogram (ECG) monitoring. Terms synonymous with DCD donor include non heart-beating donor (NHBD) and donation after cardiocirculatory death donor.

The crucial difference between the brain dead donor and the DCD donor is that warm in situ ischemia is inherent in DCD leading to significant myocardial injury (FIG. 1). The definition of warm ischemic time varies between institutions. At the Alfred Hospital, warm ischemic time is the duration between the systolic blood pressure falling below 50 mmHg and the start of cold preservation. Another common definition is the interval of time between cessation of mechanical ventilation until the initiation of cold preservation. This includes the stand-off period that is applied between cardiac arrest and declaration of patient death (typically 2 to 5 minutes). The brain dead donor encounters no such warm ischemia. Death is pronounced well in advance of donation based on neurologic criteria and the organs remain perfused by the heart until the moment cold preservation is administered.

Cold ischemic time extends from the beginning of cold preservation until the restoration of blood perfusion after transplantation and includes the period of graft implantation. This period is the same for brain dead donors and DCD donors.

It is particularly important to minimise further damage to DCD organs, since they have already been insulted by warm ischemia. The present invention addresses this need. Four types of DCD donor have been identified (Table 1).

TABLE 1

The 'Maastricht categories' of donation after cardiac death (DCD) donors.

| Category | Description | Controlled or uncontrolled |
|---|---|---|
| I | patient dead on arrival at hospital | Uncontrolled |
| II | patient who undergoes unsuccessful resuscitation | Uncontrolled |
| III | patient awaiting planned withdrawal of treatment | Controlled |
| IV | brain-dead patient who subsequently sustains cardiac arrest | Controlled |

The category III donor is the most common source of DCD organ donation. This donor has severe, irreversible brain damage with no hope of recovery but does not meet the criteria for brain death. Once informed consent is obtained for both withdrawal of life support and organ donation, mechanical ventilation and life support is withdrawn either in the ICU or operating theatre. Hypoxic cardiac arrest results and after a mandatory stand-off period, death is pronounced. Only then can organ procurement proceed. The category III donor is called a controlled DCD donor as the moment of circulatory arrest can be planned and the precise period of warm ischemia is known.

Other DCD donors include category I, II and IV donors. In category IV, the brain dead patient develops cardiac arrest during organ procurement, minutes before the initiation of cold perfusion. Hence warm ischemia is limited to only a few minutes. The category IV donor is considered a controlled DCD donor. Categories I and II are the uncontrolled DCD donors. Death is unexpected and the exact duration of warm ischemia is often unknown. This raises the question of organ viability complicating the possible application to transplant practice.

The DCD donor scenario mandates the consideration of additional factors over and above the established ethical principles of organ transplantation. The duration of observation following onset of asystole required to declare an irreversible cessation of cardiopulmonary function is controversial. On the one hand, a sufficient observation period is imperative to ensure that asystole is in fact permanent and autoresuscitation (spontaneous resumption of function) does not occur. However, the nature of the DCD process is such that reducing ischemic time is paramount to maximising the chance of recovery of donated organs and their recipients. The longest asystolic period to be followed by autoresuscitation is less than 60 seconds, a fact considered by the Institute of Medicine and the Society of Critical Care Medicine who concluded that following asystole, in order to pronounce death, 'at least 2 minutes of observation is required, and more than 5 minutes is not recommended'. It can be argued that a heart could be restarted after 2 minutes of asystole through external stimulation, however, in the setting of futility of ongoing treatment and a subsequent decision to withdraw treatment, most agree that death has occurred when cardiopulmonary function ceases and will not spontaneously resume. However, if a heart is restarted, the donor from whom it was taken cannot have been dead according to cardiac criteria. Otherwise, once the heart has arrested for more than 3 to 4 minutes, brain death has ensued and the body as a whole can never be revived.

In the early history of transplantation, grafts including kidney, liver and pancreas were obtained from DCD donors. Following the introduction of brain death however, most organs have been procured from brain dead donors. In the past 15 years, an increasing shortage of donor organs has renewed interest in the DCD donor.

Good clinical results have been achieved in transplantation of the kidneys from both controlled and uncontrolled DCD donors. Patients who receive category III DCD donor kidneys, despite having increased rates of delayed graft function resulting in longer hospital stays, are not significantly different to patients who receive brain dead donor kidneys in terms of primary graft failure and mean creatinine at 12 months. The patient and graft survival at 6 years is reported to be 83% and 80% respectively in DCD, compared to 89% and 87% respectively in brain dead donation. Transplantation of category I and II DCD donor kidneys has also shown promising results.

Transplant centres have also utilised DCD donors in liver transplantation and lung transplantation, with DCD donor lungs derived from category III donors. There are also encouraging accounts of uncontrolled DCD donor lung transplantation.

The first human heart transplant in fact used a DCD donor. However, since the inception of organ donation following brain death, clinical transplantation of DCD hearts has been rare for a number of reasons. First and foremost is the great concern over the vulnerability of the heart to warm ischemia. The heart is unlike the kidney, liver and lung which are better able to tolerate this insult. Secondly, reperfusion injury is particularly severe in the DCD heart and adds further insult to the already-damaged myocardium. Thirdly, preservation techniques have failed to provide consistent and adequate myocardial recovery of the DCD heart. Fourthly, there is no suitable method of assessing graft viability, which is vital given the potential damage a DCD heart may sustain prior to implantation.

Mechanisms of Injury

"Ischemia" means insufficient blood supply in relation to demand. It is most often due to a reduction or interruption of blood flow caused by a mechanical obstruction in the arterial vasculature leading to a decrease in the supply of oxygen and nutrients. At the onset of ischemia, oxidative phosphorylation ceases causing a reduction in ATP generation. Although the ischemic myocardium is able to continue producing ATP via anaerobic glycolysis, this process is very inefficient and is only able to yield 2 moles of ATP per mole of glucose (compared to 38 moles of ATP in aerobic conditions). Declining ATP leads to a failure of the sodium-potassium pump resulting in intracellular sodium overload and oedema. Calcium surges into the intracellular space which opens the mitochondrial permeability transition pore (MPTP) preventing ATP generation, stimulates enzymes that break down cell membranes and causes myocardial contracture and arrhythmias. The accumulation of harmful metabolites such as lactate results in tissue acidosis. These early changes are reversible if blood and oxygen supply are promptly re-established. However, if ischemia persists, irreversible injury to the tissue ensues.

The myocardium is extremely vulnerable to ischemic injury. The exact duration of ischemia that causes reversible injury to become irreversible is unknown. However, after 10 minutes of warm ischemia, canine hearts showed a 70% reduction in ATP levels, after 20 minutes warm ischemia there is evidence of irreversible damage to myocardial tissue and after a 60 minute warm ischemic interval the heart becomes hyper-contracted with no systolic function, a state referred to as 'the stone heart'. It is commonly believed that irreversible injury to the myocardium begins approximately 20 to 30 minutes after the onset of severe ischemia. Certainly the heart is very sensitive to ischemia and the damage it sustains rapidly progresses from reversible to irreversible.

The reintroduction of blood flow following a period of reduced or absent blood flow is known as "reperfusion". Timely reperfusion minimises the extent of an ischemic insult and can promote the recovery of cells which are reversibly injured. However, reperfusion itself can paradoxically aggravate and accelerate the damage sustained by ischemic tissues thus causing the death of cells that may otherwise have recovered. This is known as "reperfusion injury" or "ischemia-reperfusion injury" and is an important consideration in myocardial infarction, stroke and organ transplantation. Several mechanisms are thought to be responsible for reperfusion injury including:

1. Calcium overload. In the early stages of reperfusion, the sodium/hydrogen ($Na^+/H^+$) exchanger (NHE) attempts to correct intracellular acidosis by bringing sodium into the cell, worsening the existing sodium overload that develops during ischemia. The sodium-calcium pump subsequently exchanges sodium for calcium resulting in calcium overload and its harmful consequences.

2. Oxidative stress, reperfusion, and more specifically reoxygenation, generates reactive oxygen species (ROS), also known as free radicals. ROS directly damage cell membranes by lipid peroxidation and also damage cellular proteins, carbohydrates and DNA.

3. Activation of the complement system alters vascular homeostasis and increases leucocyte-endothelial adherence resulting in compromised blood flow.

4. Leucocyte activation causes release of ROS, proteases and elastases resulting in increased microvascular permeability, oedema, thrombosis and parenchymal cell death.

5. No-reflow phenomenon. Ischemia and reperfusion both cause vascular injury which if sufficiently severe can result in the no-reflow phenomenon in which blood flow to ischemic tissue remains impeded even after the blood supply is restored.

The donor heart is subjected to many potential sources of injury. These include brain death-induced myocardial damage, warm in situ ischemia in DCD, surgical injury, cold ex vivo ischemia during storage and reperfusion injury. Minimising the severity of each of these insults maximises the donor heart's chance of recovery (Table 2). Donor heart management is even more crucial in the DCD donor, due to the heart's poor tolerance of warm ischemia.

TABLE 2

The stages of injury to the donor heart and ways in which injury may be minimised.

| Stage of transplant | Minimisation of injury |
| --- | --- |
| 1. Prior to explantation | |
| Brain dead donor following brain death | Minimisation of myocardial damage from brain death through timely procurement |
| DCD donor following cardiopulmonary death | Minimisation of warm in situ ischemia through timely procurement |
| 2. Donor procurement | Prevention of cardiac distension Prompt and efficient delivery of cardioplegia |
| 3. Storage for transport | Optimal cardioplegia/storage solution Hypothermic perfusion preservation |
| 4. Implantation | Continued myocardial protection (frequent doses of cardioplegia) Prevention of cardiac distension |
| 5. Reperfusion | Prevention of cardiac distension |
| 6. Early postoperative period | Avoidance of excessive use of inotropes Avoidance of hypoxia |

Cardioplegic Solutions

Figure 2:
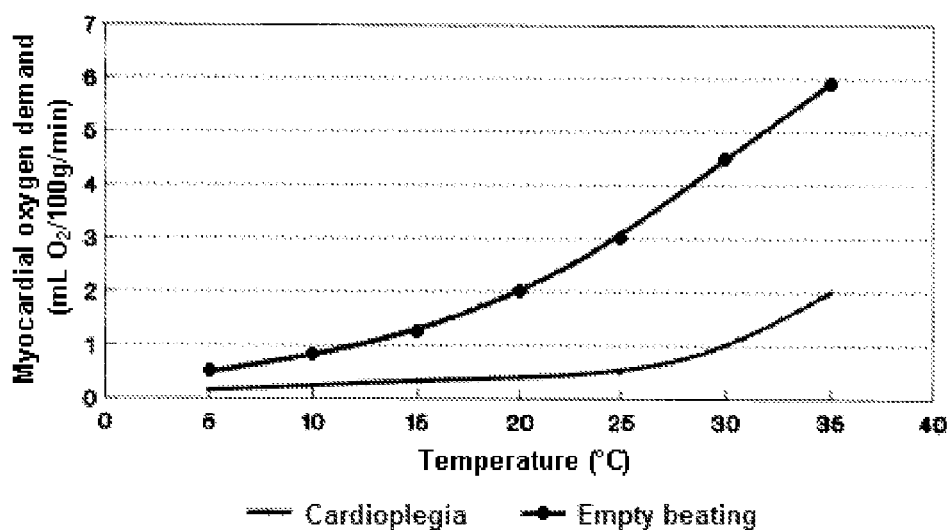
FIG. 2 is a graph depicting myocardial oxygen demand at temperatures between 5° C. and 35° C.

Cardioplegic solutionCardioplegic solutions are used in most forms of cardiac surgery including coronary artery bypass grafting, valve repair and replacement. These solutions are also used in donor heart procurement to rapidly induce cardiac arrest and reduce the temperature of the heart in order to decrease myocardial energy demand and preserve energy stores (FIG. 2).

As used herein, "cardioplegia" refers to intentional and temporary cessation of cardiac activity, generally induced using a "cardioplegic solutioncardioplegic solution" known to the person skilled in the art.

As used herein, "standard cardioplegia" refers to cardioplegia induced using a single cardioplegic solutioncardioplegic solution known to the person skilled in the art.

Many cardioplegic solutioncardioplegic solutions have been developed in an effort to optimise organ protection. These can be broadly divided into the intracellular-type and extracellular-type solutions. The former are exemplified by the University of Wisconsin (UW) solution and the latter by the St. Thomas' Hospital No. 2 and Celsior® solutions (Table 3). Intracellular-type solutions have similar ionic concentrations to the physiological intracellular space and extracellular-type solutions have similar ionic concentrations to the physiological extracellular space. There are also numerous additives that have been used in cardioplegic solutions e.g. lactobionate, raffinose and glutathione. A detailed discussion about the relative effectiveness of the various cardioplegic solutions and additives is beyond the scope of this review but following is a brief comparison of intracellular-type and extracellular-type solutions.

Intracellular solutions were originally developed for the preservation of solid organs including kidney and liver. In routine cardiac surgery however, surgeons predominantly use extracellular solutions to arrest the heart. At the Alfred Hospital, St. Thomas' Hospital No. 2 solution is the standard cardioplegia used in routine cardiac surgery as well as donor heart preservation.

TABLE 3

Composition of representative examples of intracellular-type (University of Wisconsin) and extracellular-type (St. Thomas' Hospital No. 2 and Celsior ®) cardioplegic solutions.

| Component | University of Wisconsin (UW) | St. Thomas' Hospital No. 2 | Celsior ® |
| --- | --- | --- | --- |
| Sodium | 25 mM | 110 mM | 100 mM |
| Potassium | 125 mM | 16 mM | 15 mM |
| Magnesium | 5 mM | 16 mM | 13 mM |
| Calcium | — | 1.2 mM | 0.25 mM |
| Chloride | — | 139 mM | 41.5 mM |
| Bicarbonate | — | 10 mM | — |
| Phosphate | 25 mM | — | — |
| Lactobionate | 100 mM | — | 80 mM |
| Mannitol | — | — | 60 mM |
| Raffinose | 30 mM | — | — |
| Glutathione | 3 mM | — | 3 mM |
| Hydroxy-ethyl starch | 50 g/L | — | — |
| Adenosine | 5 mM | — | — |
| Glutamate | — | — | 20 mM |
| Histidine | — | — | 30 mM |
| Insulin | 40 U/L | — | — |
| Decadron | 8 mg/L | — | — |
| Penicillin | 200,000 U/L | — | — |
| Allopurinol | 1 mM | — | — |
| pH | 7.4 (at 4° C.) | 7.8 (at 4° C.) | 7.3 (at 20° C.) |

Hypothermia reduces the energy requirements of the myocardium (FIG. 2). By reducing the metabolic rate of the ischemic heart, hypothermia slows down tissue deterioration. It has been shown that the ideal temperature for prolonged preservation (3 to 6 hours) is 4° C., although the accepted limit is 4 hours. This technique also has disadvantages including inhibition of enzyme function, interference with ATP generation and utilisation and cellular oedema.

Cold storage is the standard technique of cardiac preservation used in heart transplantation today. Following cardioplegia arrest, the heart is placed in a bag filled with cold preservation fluid for the storage period. The bag is surrounded with ice to maintain hypothermia.

As used herein, "hypothermic preservation", "cold storage preservation", "cold storage" and similar terms refer to maintenance of a donor organ at approximately 2 to 4° C., commonly using ice or ice substitutes, and without perfusion.

The strengths of cold storage are its simplicity, convenience and low cost. However, it is an imperfect technique with many limitations including a maximum safe ischemic time of 6 hours. This presents a great obstacle in transporting a heart from a geographically distant location, especially in Australia and New Zealand with donors in Australia sometimes matched to recipients in New Zealand and vice versa. Even within this time limit, as the ischemic period extends, cell integrity deteriorates and risk of myocardial dysfunction following reperfusion increases dramatically. The one year mortality rates of heart transplant recipients in whom organ ischemic times are 6 hours has been reported to be as great as double of those in whom ischemic times are 3 hours or less. In Australia and New Zealand, primary graft failure is responsible for 9% of recipient deaths.

As used herein, "standard preservation" refers to cardioplegia using a single cardioplegic solution and hypothermic preservation, also referred to as cold storage.

Perfusion preservation is the technique of perfusing an organ, ex vivo, either with a blood or crystalloid (non-blood) composition, e.g. solution, known as the perfusate. It has many benefits and has been identified as a potential method of improving the preservation of various organs including kidney, liver, pancreas, lung and heart.

As used herein, "perfusion" refers to the process of delivery to a capillary bed in the donor organ of nutrients provided in a "perfusion composition" or "perfusate".

In hypothermic perfusion preservation of the heart, perfusates are based on cardioplegic solutions with various additives designed to preserve the integrity of the myocardium. Both intracellular and extracellular solutions have been used.

As used herein, "hypothermic perfusion preservation", "hypothermic perfusion", "cold perfusion" and similar terms refer to preservation of a donor organ by maintenance of the organ at approximately 0 to 10° C. coupled with perfusion. The perfusate or perfusion composition may comprise solely blood, a solution comprising blood, or a non-blood solution. Cardioplegia may be standard cardioplegia using a single cardioplegic solution known to the person skilled in the art or may be two-part cardioplegia using two cardioplegic solutions as disclosed herein.

Experimental evidence suggests that hypothermic perfusion preservation may improve donor heart preservation compared to cold storage. It prolongs the safe ischemic time which allows the accessing of organs from greater distances and the opportunity for better donor/recipient tissue matching before transplant. A continuous supply of substrate and oxygen over ischemic times varying from 4 to 24 hours allows aerobic metabolism to proceed which better protects myocardial ATP stores and tissue pH compared to cold storage. Oxidative stress, damage to DNA and apoptosis are also reduced. Hypothermic perfusion preservation reduces lactate production suggesting that these hearts can utilise the provided substrates and oxygen for aerobic metabolism. Finally, hypothermic perfusion preservation improves graft function after both short and long storage intervals.

Tissue oedema is a primary concern of perfusion preservation. Early studies showed a five-fold higher degree of weight gain in perfused hearts compared to hearts preserved with cold storage. In perfusion preservation the development of oedema can cause an increase in coronary resistance due to vessel compression, resulting in impaired circulation and suboptimal myocardial protection. However, oedema can be reversible and a small amount of oedema may not necessarily impair heart function. Better understanding of the mechanisms involved in oedema has allowed the present perfusion method to be altered to minimise this problem e.g. lower perfusion rates and addition of oncotic agents to perfusates.

Despite evidence that hypothermic perfusion preservation provides better myocardial recovery than cold storage, transplant units have continued using cold storage as the standard technique for donor heart preservation. This is because cold storage is simple, safe, predictable, inexpensive and provides adequate protection of the standard donor heart if ischemia is restricted to 4 hours. Also, the heterogeneous nature of existing techniques and restricted clinical application of hypothermic perfusion preservation means the optimal protocol for perfusion preservation of the heart is still undetermined. However, the concerted effort to expand the donor pool by utilising marginal and DCD donors has renewed interest in perfusion preservation as a technique for preserving these damaged organs.

Cold storage in ice may be adequate for preservation of standard brain dead donor hearts up to 4 hours, however, the DCD heart sustains a severe warm ischemic insult during the agonal period and thus any further damage is much more likely to cause irreversible injury. An early study subjected pig hearts to warm ischemic periods varying between 0 and 60 minutes followed by 2 hours of cold storage. The authors concluded that hearts procured 10 minutes or greater after death and then cold stored were unable to be resuscitated and were unsuitable for transplantation. A subsequent study from our unit demonstrated in a canine model that hearts left untouched for 30 minutes following cessation of ventilation and subjected to 4 hours of cold storage recovered very poorly. Functional recovery can be improved experimentally with administration of donor pretreatments. However, although donor pretreatments such as methylprednisolone, dextrose, nifedipine, and prostaglandin E1 may be desirable for optimal organ protection, they are ethically unacceptable because they are of no benefit to the donor and therefore not suitable clinically.

Attempts have been made to find a suitable alternative to cold storage for preservation of the DCD heart. Perfusion with "blood cardioplegia" (a mix of whole blood and cardioplegic solution) and/or whole blood has been tested with mixed success. Studies to date suggest that DCD hearts may be able to recover sufficiently for transplantation if perfused with blood cardioplegia and/or whole blood. However, as noted previously, this is technically demanding and expensive.

Another form of hypothermic perfusion preservation uses crystalloid (non-blood) composition, e.g. solutions, that differ from modified cardioplegic solutions. So-called "hypothermic crystalloid perfusion" of the DCD donor heart has been tested only in animal models in which death was induced by exsanguination, which is not relevant to the DCD donor.

As used herein, "hypothermic crystalloid preservation" refers to "hypothermic perfusion preservation" in which the perfusion composition or perfusate is a non-blood composition, e.g. a solution.

Clinical experiences with DCD heart reanimation and transplantation are rare. Three successful paediatric DCD heart transplants have been reported. The mean time to death in donors after withdrawal of life support was 18.3 minutes, the stand-off period before initiation of preservation techniques was between 1.25 and 3 minutes, and the mean total ischemic time 162 minutes. Although the small number of patients limits the conclusions that can be drawn, compared to a control group of 17 infants who received transplants procured through standard organ donation, at 6 months post transplant, the DCD heart transplant recipients had a greater survival (100% vs 84%), similar number of rejection episodes and comparable cardiac function measured on echocardiogram. Two attempts at preserving human hearts from controlled DCD donors with ex vivo evaluation on an isolated working heart apparatus have been reported. One heart recovered full function with blood reperfusion after 23 minutes of warm hypoxia, whilst the other heart, despite a shorter warm ischemic time of 17 minutes, showed poor functional recovery. These preliminary experiences with human DCD donor hearts support future research and development in the field of DCD donor heart transplantation.

The regular technique in clinical practice for donor heart preservation of cold storage in ice provides adequate protection for the standard brain dead donor heart for ischemic times up to 4 hours. However, the DCD donor heart, which receives a severe warm ischemic insult during the process of death, recovers poorly if preserved by cold storage. On the other hand, normothermic blood perfusion allowed the DCD heart to recover function suitable for transplantation. There is a commercial machine available for clinical blood perfusion of the donor heart, but has had limited clinical application in heart transplantation of brain dead donor hearts, and apparently no application in DCD heart transplantation. Unfortunately this complex machine usually costs $100,000 to acquire and also requires $50,000 worth of disposables with each use. This prohibitive cost severely limits the application of blood perfusion to regular clinical practice. Perfusion can also be delivered at hypothermic temperatures using a crystalloid (non-blood) composition, e.g. solution. This technique is potentially more cost-effective and simpler than blood perfusion, and has been demonstrated to be effective in normal hearts. Although existing studies on hypothermic crystalloid perfusion of DCD donor hearts have provided encouraging results, these were conducted under conditions not applicable to clinical practice. This method of preservation has not been carried out in a model that mirrors the majority of clinical DCD donation, that is, Maastricht category III DCD donation. Table 4 compares cold storage, normothermic blood perfusion and hypothermic crystalloid perfusion for preservation of the donor heart.

TABLE 4

Comparison of cold storage, normothermic blood perfusion and hypothermic crystalloid perfusion for preservation of the heart.

|  | Cold storage | Normothermic blood perfusion | Hypothermic crystalloid perfusion |
|---|---|---|---|
| Technique | Cardioplegia arrest and immersion in cold preservation solution | Perfuse coronary arteries with whole blood at warm temperature | Perfuse coronary arteries with non-blood composition at cold temperature |
| Metabolism | Anaerobic | Aerobic | Aerobic |
| Waste products | Accumulate | Washed out | Washed out |
| Application in brain-dead donor hearts | Standard practice but safe ischemic period limited to 4 to 6 hours | Rarely used | Rarely used |
| Recovery of DCD donor hearts | Inadequate | Adequate | Literature is encouraging but not yet tested in a clinically-applicable model |
| Cost and complexity | Simple and inexpensive | Highly complex and very expensive | Simple and relatively inexpensive |

Without wishing to be bound to any particular hypothesis, the inventors consider the following components and their proposed mechanisms to be the basis for the perfusion composition and method of the invention.

Two-Part AMPI Cardioplegia

In the DCD donor, although cardiac arrest is induced by hypoxia, the inventors have utilised "acidic mitochondrial pore inhibiting" cardioplegia that has a role in cooling the heart, supplying metabolic substrates and reducing reperfusion injury. Hypothermic crystalloid perfusion as disclosed herein utilised two-part cardioplegia, which is distinct from standard cardioplegia. Both parts are based on St. Thomas' Hospital No. 2 (Table 3) cardioplegia with additives and modifications including:

Aspartate, an amino acid that stimulates ATP production. Aspartate may improve functional recovery of the heart as measured by both aortic flow and cardiac output. Aspartate may maintain ionic integrity of myocardial tissue and is an important intermediary metabolite in the heart. Aspartate may aid transport of minerals and nutrients to the cells. Aspartate may also counteract the excitotoxicity when high levels of calcium ions enter the cells during the period when the ATPase pump is disrupted. Glutamate may be used as an alternative to aspartate. In one embodiment, the cardioplegic solution comprises 14 mM aspartate or glutamate. In another embodiment, the cardioplegic solution comprises 20 mM aspartate or glutamate. In other embodiments, the cardioplegic solution may comprise 1, 2, 3, 4, 5, 6, 7, 8, 9, 10, 11, 12, 13, 15, 16, 17, 18, 19, 21, 22, 23, 24, 25, 26, 27, 28, 29, 30, 31, 32, 33, 34, 35, 36, 37, 38, 39, or 40 mM aspartate or glutamate. Aspartate and glutamate may be provided as a $K^+$ or $Na^+$ salt.

Adenosine causes vasodilation of the coronary arteries via the A2B adrenergic receptors thereby decreasing coronary vascular resistance. Adenosine also may reduce lactate accumulation and improve function. A vasodilator may increase the permeability of the cellular membrane. Adenosine is a hyperpolarized mediated calcium channel blocker, affecting the level of intracellular calcium thereby decreasing intracellular calcium. Adenosine also increases the ATP-sensitive potassium channel, which stabilizes membrane potential during ischemic events. Adenosine prevents peripheral vasoconstriction in the coronary circulation during long term perfusion as it also increases the store of high energy phosphates in heart muscle and thus facilitates the restoration of metabolism on reperfusion. Other vasodilators can be used in the cardioplegic solution, for example cyclic adenosine monophosphate (cAMP) and cyclic guanosine monophosphate (cGMP), which also have positive effects on glycolytic activity. In one embodiment, the cardioplegic solution comprises 5 µM adenosine, cAMP or cGMP. In other embodiments, the cardioplegic solution may comprise 1, 2, 3, 4, 6, 7, 8, 9, 10, 11, 12, 13, 14, 15, 16, 17, 18, 19, 20, 21, 22, 23, 24, or 25 µM adenosine, cAMP or cGMP. Alternatively, the cardioplegic solution may comprise 1, 2, 3, 4, 5, 6, or 7 mg/L adenosine, cAMP or cGMP.

Insulin may be included in the cardioplegic solution. In one embodiment, the cardioplegic solution comprises 100 U/L insulin. In other embodiments, the cardioplegic solution may comprise 10, 20, 30, 40, 50, 60, 70, 80, 90, 110, 120, 130, 140, 150, 160, 170, 180, 190, or 200 U/L insulin.

Cyclosporine is a mitochondrial permeability transition pore (MPTP) inhibitor that improves post-ischemic function by protecting mitochondria from ischemia/reperfusion injury and reduces the ischemic release of lactate dehydrogenase and troponin I. Acidosis during early reperfusion prevents MPTP formation, thus reducing oxidative stress and reperfusion injury. In one embodiment, the cardioplegic solution comprises 5 mg/L cyclosporine. In other embodiments, the cardioplegic solution may comprise 1, 2, 3, 4, 6, 7, 8, 9, or 10 mg/L cyclosporine.

Cariporide is a sodium/hydrogen ($Na^+/H^+$) exchanger (NHE) inhibitor which may improve the recovery of perfused donor organs, for example DCD donor hearts. Alternatively, amiloride or another sodium-hydrogen exchange inhibitor may be incorporated into the cardioplegic solution. In one embodiment, the cardioplegic solution comprises 3.79 mg/L cariporide. In other embodiments, the AMPI cardioplegic solution may comprise 1, 2, 3, 4, 5, 6, 7, or 8 mg/L cariporide.

Oxygen facilitates aerobic metabolism and may be bubbled into the cardioplegic solution using 80% $O_2$.

The preferred pH of the cardioplegic solution is 7.2. This acidic pH has been shown to protect mitochondria. In another embodiment, the pH of the cardioplegic solution may be 7.1, 7.11, 7.12, 7.13, 7.14, 7.15, 7.16, 7.17, 7.18, 7.19, 7.21, 7.22, 7.23, 7.24, 7.25, 7.26, 7.27, 7.28, 7.29, or 7.3.

Perfusion Composition

The perfusion composition of the invention was recently developed as a perfusate for donor heart perfusion, but may be used for perfusing a kidney, a lung, a liver or a pancreas. It is similar to extracellular cardioplegic solutions and has various additives. The perfusion composition will keep an ischemic heart in a condition to successfully survive to transplant for 12 hours or more. In other embodiments, the perfusion composition will preserve the donor organ for 1, 2, 3, 4, 5, 6, 7, 8, 9, 10, 11, 13, 14, 15, 16, 17, 18, 19, 20, 21, 22, 23, 24, 25, 26, 27, 28, 29, 30, 31, 32, 33, 34, 35, 36 or more hours after harvest. A summary of the formulation of the perfusion composition follows.

As one of the main issues in maintaining cell life ex vivo during a period of ischemia is the prevention of the lethal changes in cellular hydration and chemistry, and this perfusion composition "normalizes" as much as possible the cellular functions, including the sodium/calcium/potassium balance.

Preharvest or prior to ischemia, the sodium-potassium adenosine triphosphatase (Na—K ATPase) pump functions to maintain the ionic composition of the cell. The pump is disrupted by ischemia because of the lack of ATP production and by excessive production of hydrogen ions because of anaerobic metabolism during ischemia. Under ischemic conditions, there is a switch from aerobic to anaerobic glycolysis, and the production of lactic acid increases. When the sodium-potassium ATPase pump is disrupted, potassium moves out of the cell, whereas sodium, which is normally kept at a low concentration in the cell, pours in. This ionic shift causes cell swelling and disruption of the cell if unchecked. Calcium influx into cells activates a number of enzymes, including phospholipases, endonucleases, and proteases such as calpain. These enzymes go on to damage cell structures such as components of the cytoskeleton, membrane, and DNA. Hydrogen-ion production continues in ischemic organs and causes intracellular pH to decrease without replenishment of buffering capabilities. Calcium ion permeability is increased with ischemia, and a rapid influx of calcium overpowers the intracellular buffering capacity.

Nevertheless, calcium ($Ca^{2+}$) is incorporated in a lower concentration into the perfusion composition as a countering agent to the potassium in the composition. In a normal depolarized heart, the interaction between potassium and calcium works in the contraction of the heart muscle through the excitation of the muscle fibres of the heart. In one embodiment, the perfusion composition comprises 0.5 mM calcium. In another embodiment, the perfusion composition may comprise 0.1, 0.2, 0.25, 0.3, 0.4, 0.6, 0.7, 0.75, 0.8, 0.9 or 1.0 mM calcium. In one example, the source of $Ca^{2+}$ is calcium chloride.

Potassium ($K^+$) stabilizes the cellular structure for the prevention of hypokalemia during ischemia, which can lead to cellular oedema as sodium will replace the potassium lost during the anaerobic metabolism of ischemia. In one embodiment, the perfusion composition comprises 15 mM potassium. In another embodiment, the perfusion composition may comprise 1, 2, 3, 4, 5, 6, 7, 8, 9, 10, 11, 12, 13, 14, 16, 17, 18, 19, 20, 21, 22, 23, 24, 25, 26, 27, 28, 29, or 30 mM potassium. In one example, the source of $K^+$ is potassium chloride.

As indicated above in respect of the two-part cardioplegic solution, a sodium/hydrogen ($Na^+/H^+$) exchanger (NHE) inhibitor will also aid in potassium retention by the heart cells, along with reducing the damage from anoxia and reperfusion injury after transplant.

The perfusion composition comprises a high concentration of magnesium ($Mg^{2+}$) relative to the concentration of calcium to keep the heart in hyperpolarized arrest and help preserve the heart muscle cell membrane so that membrane excitability is better restored after transplantation. Magnesium acts as a calcium antagonist, thus preventing calcium overload. Magnesium is also present to stabilize the myocardial membrane by inhibiting a myosin phosphorylase, which protects ATP reserves for post-ischemic activity. Magnesium is regulates and balances the sodium-potassium-calcium pump of the heart cells. Magnesium is also present to counteract lactic acidosis associated with ischemia. Low magnesium compromises the integrity of the cell wall causing lesions. In one embodiment, the perfusion composition comprises 7.5 mM of magnesium. In another embodiment, the perfusion composition may comprise 1, 2, 3, 4, 5, 6, 7, 8, 9, 10, 11, 12, 13, 14, or 15 mM magnesium. In one example, the source of $Mg^{2+}$ is magnesium chloride.

The concentration of sodium ($Na^+$) in the perfusion composition maintains integrity of the cell membrane to lower the likelihood of calcium paradox during reperfusion. In one embodiment, the perfusion composition comprises 80 mM sodium. In another embodiment, the perfusion composition may comprise 10, 20, 30, 40, 50, 60, 70, 90, 100, 110, 120, 130, 140, 150, or 160 mM sodium. In one example, the source of $Na^+$ is sodium chloride.

Chloride ($Cl^-$) may be present as a counter ion to maintain the electroneutrality of the composition. The source of $Cl^-$ may be derived from the source of any one or more of the sources of $Ca^{2+}$, $Mg^{2+}$, $K^+$, or $Na^+$.

As understood by the person skilled in the art, salts other than chloride salts may be the source of $Ca^{2+}$, $Mg^{2+}$, $K^+$, or $Na^+$. However, insoluble salts of $Ca^{2+}$ and $Mg^{2+}$ are to be avoided. In one example, the counter ion for the source of $Ca^{2+}$, $Mg^{2+}$, $K^+$, or $Na^+$ is gluconate. The person skilled in the art will appreciate that the salt sources of $Ca^{2+}$ and $Mg^{2+}$, for example, may be hydrates.

Glucose and insulin promote glycolysis and ATP production and may improve recovery of perfused hearts. Prolonged survival of cardiac muscle at 4° C. depends on glycolysis that utilizes the muscle glycogen stores and produces lactic acid and other metabolites that produce $CO_2$. By including glucose and insulin, the cell is able to take up and metabolize glucose, thereby preserving the cellular glycogen stores that will not require replenishing after transplanting the organ. Although glucose is not the major metabolic substrate in the heart at rest, there are circumstances in which it assumes greater importance, such as during ischemia. Glucose assumes a central role for energy production in the ischemic heart, when lack of oxygen induces a shift to anaerobic metabolism with rapid stimulation of glucose uptake, glycogenolysis, and glycolytic flux. The damage that results from ischemia includes the inability to dispose of the products of glycolysis (such as lactate), and the damaging effects of oxygen-derived free radicals on enzymes and cellular membrane phospholipids.

Although glucose has often been used in Krebs-Henseleit perfusion composition for Langendorff perfusions, it has not been used in "preservation" compositions or solutions, because excessive glucose in an ischemic heart can promote excess lactate production.

In one embodiment, the perfusion composition comprises 14 mM glucose. In another embodiment, the perfusion composition may comprise 1, 2, 3, 4, 5, 6, 7, 8, 9, 10, 11, 12, 13, 15, 16, 17, 18, 19, 20, 21, 22, 23, 24, 25, 26, 27, 28, 29, or 30 mM glucose. In another embodiment, fructose or mannitol may be used as an alternative to glucose. Fructose releases its energy more slowly than glucose and, in contrast to glucose, does not need insulin for metabolism. Mannitol can serve three purposes as: a glucose substitute; a free radical or ROS scavenger; an oncotic colloidal agent.

Insulin may be a component of the perfusion composition, at a lower concentration than in the cardioplegic solution, and is used to enhance the uptake of glucose into heart muscle cells. Insulin has a direct positive inotropic effect on the reperfused heart. Insulin also promotes glucose utilization and oxidation increased during reperfusion. Insulin also inhibits programmed cell death (apoptosis). Insulin, when combined with glucose and potassium, as in this invention, also attenuates myocardial reperfusion injury and thus may exert significant cardioprotection in patients who receive reperfusion. In one embodiment, the perfusion composition comprises 6 Units of short-acting or regular insulin. In another embodiment, the perfusion composition may comprise 1, 2, 3, 4, 5, 7, 8, 9, 10, 11, 12, 13, 15, 16, 17, 18, 19, 20 Units of short-acting or regular insulin. In another embodiment, the perfusion composition may comprise an intermediate-acting insulin such as NPH or a long-acting insulin or analogue thereof such as ultralente. Alternatively, the perfusion composition may comprise a combination of short-acting, intermediate-acting and/or long-acting insulin. The insulin may be human or porcine. The insulin may be recombinant. Preferably, the insulin is non-aggregating.

Fructose-1,6-diphosphate (FDP) may adsorb to and stabilize the cell membrane the membrane. In one embodiment, the perfusion composition comprises 2 mM FDP. In another embodiment, the perfusion composition may comprise 0.2, 0.4, 0.6, 0.8, 1, 1.2, 1.4, 1.6, 1.8, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, or 10 mM FDP. FDP may be provided as a sodium or potassium salt.

Aspartate, or a substitute, may be incorporated into the perfusion composition at the same or similar concentration as incorporated into the cardioplegic solution above.

Adenosine, or a substitute, may be incorporated into the perfusion composition at the same or similar concentration as incorporated into the cardioplegic solution above. In one embodiment, the perfusion composition comprises 5 mM adenosine, cAMP or cGMP. In other embodiments, the perfusion composition may comprise 1, 2, 3, 4, 6, 7, 8, 9, 10, 11, 12, 13, 14, 15, 16, 17, 18, 19, 20, 21, 22, 23, 24, or 25 mM adenosine, cAMP or cGMP. Alternatively, the perfusion composition may comprise 1, 2, 3, 4, 5, 6, or 7 g/L adenosine, cAMP or cGMP.

The perfusion composition may comprise reduced glutathione (GSH), which functions as a reducing agent and a free radical scavenger. It is known that free radicals play an important role in reperfusion-induced cellular and organ damage and that abrupt reperfusion of the ischemic myocardium can lead to massive formation of ROS. Agents known to scavenge or inhibit the formation of free radicals can prevent reperfusion-induced injury. GSH is a cofactor for the enzymatic destruction of hydrogen peroxide and other organic hydroperoxides. While all cells in the human body are capable of synthesizing glutathione, liver glutathione synthesis has been shown to be essential to the normal functioning of the human body. It has been shown that relatively high concentrations of up to 5 mM of glutathione are stored in the cells in the liver. Thus, the harvested organ, other than liver, is without its major source of this endogenous antioxidant, which participates directly in the neutralization of free radicals and ROS. GSH may optimise enzyme function and may improve diastolic function, coronary flow and cardiac output. In one embodiment, the perfusion composition comprises 3 mM GSH. In another embodiment, the perfusion composition may comprise 0.5, 1, 1.5, 2, 2.5, 3.5, 4, 4.5, 5, 5.5, 6, 6.5, 7, 7.5, 8, 8.5, 9, 9.5, or 10 mM GSH.

The regulation of hydrogen ions ($H^+$) is crucial as it affects the activity of many biological enzymes and thus cell function. There are several defences against pH disturbances in the body, one being the presence of buffers i.e. substances that reversibly bind $H^+$. During ischemia, the heart becomes acidotic which can impair ventricular contractility, and if sufficiently severe and prolonged leads to protein denaturation and irreversible cellular injury. Perfusion preservation has been shown to better maintain myocardial pH at physiological levels than cold storage.

Tris(hydroxymethyl)aminomethane hydrochloride (Tris or THAM) is used a buffer, that has an effective pH range between 7.0 and 9.2, which counteracts the occurrence of metabolic acidosis. Tissues in the ischemic heart resort to anaerobic metabolism in the absence of oxygen and significant amounts of lactic acid are released into the muscle tissue and into the surrounding intercellular fluid. Tris counteracts the presence of the acid to maintain the proper pH of both the heart cell and perfusate. In one embodiment, the perfusion composition comprises 20 mM Tris or HEPES, MOPS, MES, BES or TES. In another embodiment, the perfusion composition may comprise 4-(2-hydroxyethyl)-1-piperazineethanesulfonic acid (HEPES), 3-(N-morpholino)propanesulfonic acid (MOPS), 2-(N-morpholino)ethanesulfonic acid (MES), N,N-bis-(2-hydroxyethyl)-2-aminoethansulfonic acid (BES), or N-tris(hydroxymethyl)methyl-2-aminoethanesulfonic acid (TES). In other embodiments, the perfusion composition may comprise 1, 2, 3, 4, 5, 6, 7, 8, 9, 10, 11, 12, 13, 15, 16, 17, 18, 19, 21, 22, 23, 24, 25, 26, 27, 28, 29, 30, 31, 32, 33, 34, 35, 36, 37, 38, 39, or 40 mM Tris, HEPES, MOPS, MES, BES or TES.

Bicarbonate (hydrogen carbonate, $HCO_3^-$) is used to combat metabolic acidosis, which produces lactic acid and a build-up of $CO_2$, by controlling extracellular acidosis and is used to regulate hyperkalemia, as potassium levels are brought into balance during the beginnings of ischemia. Bicarbonate fosters the $CO_2$-bicarbonate exchange at the heart muscle cell membrane which is important to cell viability. In one embodiment, the perfusion composition comprises 20 mM bicarbonate. In another embodiment, the perfusion composition comprises 1, 2, 3, 4, 5, 6, 7, 8, 9, 10, 11, 12, 13, 15, 16, 17, 18, 19, 21, 22, 23, 24, 25, 26, 27, 28, 29, 30, 31, 32, 33, 34, 35, 36, 37, 38, 39, or 40 mM bicarbonate. In two examples, the source of $HCO_3^-$ is $K\,HCO_3$ or $Na\,HCO_3$.

In one embodiment, the pH of the perfusion composition is 7.3. In other embodiments, the pH of the perfusion composition may be 7.2, 7.21, 7.22, 7.23, 7.24, 7.25, 7.26, 7.27, 7.28, 7.29, 7.31, 7.32, 7.33, 7.34, 7.35, 7.36, 7.37, 7.38, 7.39, or 7.4.

Interstitial oedema is one of the potential drawbacks of organ perfusion preservation. Oncotic pressure of a perfusate should match that of the interstitial tissue in order to minimise fluid shift into the interstitium. Blood contains albumin and globulins that provide oncotic pressure in vivo and in blood-based perfusion compositions. However, crystalloid (non-blood) perfusates do not have these natural oncotic agents. The use of non-blood perfusates without added colloid greatly increases the risk of tissue oedema. This risk can be lessened by providing lower perfusion pressures however, this subjects the organ to the possibility of inadequate and uneven tissue perfusion. Another factor contributing to the development of tissue oedema is a lack of lymphatic flow, a means by which a small amount of fluid usually returns from the interstitium back to the circulation.

The perfusion composition of the invention comprises lactobionate, a semi permeable compound, to reduce interstitial oedema. In one embodiment, the perfusion composition comprises 70 mM lactobionate and/or mannitol. In another embodiment, the perfusion composition may comprise 10, 20, 30, 40, 50, 60, 80, 90, 100, 110, 120, 130, 140, or 150 mM lactobionate and/or mannitol.

The fluid distribution between intracellular and extracellular spaces is determined mainly by the osmotic effect of solutes in both compartments. Normal osmolarity of the body fluids is 280 to 300 mOsm/L. In one embodiment, the perfusion composition is iso-osmotic and the osmotic pressure is 280, 290 or 300 mOsm/L. In another embodiment, the perfusion composition is hyperosmotic and the osmotic pressure is 310, 320, 330, 340, 350, 360, 370 or 380 mOsm/L.

Oxygenation of donor organs during preservation is a crucial factor in subsequent graft recovery, even more so in DCD donor organs. Adequate oxygenation has been shown to be much more important than supply of substrate or washout of waste in the preserved kidney. The perfusion composition of the invention may be supplemented with oxygen by direct bubbling with 80%, 90% or 100% oxygen. Oxygenation may be achieved by supplying oxygen to the perfusion composition, shaking the perfusion composition, venting the perfusion composition and repeating once, twice or more. During each round of shaking, the supplied oxygen will equilibrate with the perfusion composition, with each round of supply, shaking and venting increasing the oxygen concentration of the perfusion composition. In one embodiment, the perfusion composition is 100% saturated with oxygen. In another embodiment, the oxygen saturation may be 50, 60, 70, 80 or 90% saturated with oxygen. In other embodiments, the perfusion composition may comprise a $pO_2$ of 200, 300, 400, 500 or 600 mmHg.

Table 5 provides the final composition of one embodiment of the perfusion composition.

TABLE 5

Final composition of one embodiment of the perfusion composition.

| Component | Concentration | Purpose |
| --- | --- | --- |
| Sodium | 80 mM | Maintenance of cardiac arrest and prevention of calcium influx |
| Potassium | 15 mM | |
| Calcium | 0.5 mM | |
| Magnesium | 7.5 mM | |
| Tris | 20 mM | pH buffering |
| Sodium bicarbonate | 20 mM | |
| Glucose | 14 mM | Provision of metabolic substrate |
| Insulin | 6 Units | |
| Aspartate | 20 mM | |
| Adenosine | 5 mM | |
| Fructose-1,6-disphosphate | 2 mM | |
| Sodium lactobionate | 70 mM | Reduction of interstitial oedema |
| Glutathione (reduced) | 3 mM | Antioxidant action |
| Oxygen | 100% saturation or $pO_2$ 500 mm Hg | Facilitation of aerobic metabolism |
| pH | 7.3 | Regulation of acid-base status of myocardium |

TABLE 5-continued

Final composition of one embodiment of the perfusion composition.

| Component | Concentration | Purpose |
| --- | --- | --- |
| Osmolarity | 330 mOsm/L | Reduction of intracellular oedema |

The question of whether perfusate flow should be delivered in a pulsatile or non-pulsatile manner is an important consideration in ex vivo organ perfusion. Pulsatile pumps are complex, expensive and heavy and it would be a considerable economical advantage to employ a simpler pump if possible. The perfusion composition of the invention may be perfused using a pulsatile pump, a non-pulsatile pump, or gravity.

The perfusion composition of the invention may be perfused with a low flow rate or by microperfusion. As used herein, "microperfusion" refers to a flow rate of 2 to 8 mL/100 g/min. In one embodiment, the perfusion composition is microperfused at a rate of 4 or 5 mL/100 g/min (20 mL/min). In another embodiment, the perfusion composition may be microperfused at a rate of 2, 3, 4, 6, 7, or 8 mL/100 g/min.

The perfusion composition may be perfused through the donor organ at a pressure at the aortic root of 2 to 10 mmHg. In one embodiment, the pressure at the aortic root may be 4 to 8 mmHg. In another embodiment, the pressure at the aortic root may be 5 to 7 mmHg. The mean pressure at the aortic root during perfusion may be 1, 2, 3, 4, 5, 6, 7, 8, 9, 10, 11, or 12 mmHg.

As used herein, "controlled reperfusion" refers to the technique of modifying conditions (e.g. temperature, pressure etc.) when initially reperfusing ischemic tissue. Controlled reperfusion has been shown to reduce reperfusion injury in the heart, lung, brain and extremities. Techniques which have demonstrated benefits include:
Leucocyte depletion;
Tepid temperature between 20 to 26° C. and low perfusion pressure between 15 to 40 mm Hg; and
Initial low oxygen tension (approximately 60-70 mm Hg).

In one embodiment, components that are less stable than other components of the perfusion composition are kept separate from the other components and are added to the other components prior to use of the perfusion composition. The less stable components that may be added prior to use of the perfusion composition comprise insulin, FDP and GSH. These components may be added separately to the other components. Alternatively, one or more of the less stable components may be added simultaneously to the other components. For example, the less stable components may be formulated in a second composition to be combined with a first composition comprising the other components, thereby producing the perfusion composition. In one embodiment, FDP and GSH may be formulated in one composition, with insulin added to either the FDP plus GSH composition or to the other components just before use of the perfusion composition.

When two or more compositions, e.g. solutions, are to be combined to produce the perfusion composition, each may be buffered appropriately to produce the correctly buffered perfusion composition.

Thus, the perfusion composition may be provided in two or more parts, for example in a kit, separated until use. Preferably, once combined, the perfusion composition should be used within 48 hours.

The cardioplegic solutions may be provided in a concentrated form that is dilutable to prepare the cardioplegic solutions for use. Likewise, the perfusion composition may be provided in a concentrated form that is dilutable to prepare the perfusion composition for use.

The cardioplegic solutions and the perfusion composition may be provided in unit dose form. For example, the cardioplegic solutions and the perfusion composition may be provided in a syringe, bottle, vial, ampoule or bag. Multiple unit doses may be used in the method of the invention depending upon the duration of perfusion and flow rate of perfusion.

In one embodiment, in which less stable components of the perfusion composition are separated from the other components, the less stable components may be provided in a syringe, or may be provided in a bottle, vial, ampoule or bag and transferred to a syringe, and then injected into a bag, for example, containing the other components of the perfusion composition to prepare the perfusion composition for use. In one embodiment, the bag is a gravity-fed, drip-style bag.

Similarly, a concentrate of the cardioplegic solutions or the perfusion composition may be provided in a syringe, bottle, vial, ampoule or bag.

The person skilled in the art will understand how to prepare the cardioplegic solutions, the perfusion composition or concentrates thereof. In one brief example, the components are added to de-ionised water to a volume of 800 mL. At this point, the pH is measured and adjusted using sodium hydroxide or hydrochloric acid to 7.3+/−0.15 at 22.5° C. Once the pH has been adjusted, water is added to a volume of 1000 ml. The pH may be again checked and adjusted if needed. At 4° C., the heart produces lactic acid via glycolysis. The pH of the perfusion composition is adjusted to a slightly more alkaline pH than usual to neutralize the lactic acid.

Similarly, the stock composition may be diluted with a diluent. Preferably, the diluent is water. In another example, the diluent may be sodium chloride solution (saline) or potassium chloride solution, provided that the diluent is accounted for as a source of $Na^+$ or $K^+$ and $Cl^-$ in the perfusion composition.

Preferably, the cardioplegic solutions and the perfusion composition are sterile. As known to the person skilled in the art, sterilisation may be achieved without difficulty by moist heat sterilisation, dry heat sterilisation, chemical cold sterilisation, radiation sterilisation or filter sterilisation.

Preferably, the cardioplegic solutions and the perfusion composition are free of pyrogen and endotoxin, which may be achieved by dry heat sterilisation, for example.

The cardioplegic solutions and the perfusion composition may comprise an antibacterial drug. For example, the cardioplegic solution and the perfusion composition may comprise: a bacterial wall synthesis inhibitor (e.g. a penicillin, a cephalosporin, a carbapenem, or vancomycin); an agent that damages the cytoplasmic membrane (e.g. a polymixin); an agent that modifies synthesis or metabolism of a nucleic acid (e.g. a quinolone, rifampin, or nitrofurantoin); a protein synthesis inhibitor (e.g. an aminoglycoside, a tetracycline, chloramphenicol, erythromycin, or clindamycin); or a folate inhibitor or agent that modifies energy metabolism (e.g. a sulphonamide, or trimethoprim).

As used herein, "kit" refers to a physical arrangement of items. Thus, the items may comprise the cardioplegic solutions and/or the perfusion composition(s), which may be presented in the form of a kit. The cardioplegic solutions and/or the perfusion composition(s) of the kit may be "ready to use" in unit dose form. Alternatively, the cardioplegic solutions and/or the perfusion composition may be presented in concentrated form for dilution prior to use. The perfusion composition may be divided into less stable components and other components, again either "ready to use", other than combining, in unit dose form, or in concentrated form for diluting and combining. Where necessary for preparation of the perfusion composition, diluting and combining may be performed in any order.

The kit may be accompanied by instructions or directions to dilute a stock where necessary, combine stocks and/or compositions where necessary, and perfuse a donor organ. Additionally, or alternatively, the kit may be accompanied by instructions or directions to use the kit in a method for preserving a donor organ for transplantation according to the invention. Likewise, the perfusion apparatus of the invention may be used according to the method of the invention.

As used herein, the perfusion composition, perfusion stock composition, kit or apparatus of the invention may be defined in alternative forms. One form designates either suitability for or restriction to a specific use and is indicated by the word "for". Another form is restricted to a specific use only and is indicated by the words "in use" or "when used for" or similar.

As used herein, a "method" of preserving a donor organ for transplantation may be defined in alternative forms.

In one example, the method may be defined in the form of "use" of selected components for preserving a donor organ for transplantation.

In another example, the method may be defined in the "Swiss" style, e.g. use of selected components in the manufacture of a perfusion composition for preserving a donor organ for transplantation.

In a third example, the method may be defined in the "agent for use" form, e.g. a perfusion composition comprising selected components for use in preserving a donor organ for transplantation.

As used in herein, the singular forms "a", "an" and "the" include plural aspects unless the context clearly dictates otherwise.

As used herein, except where the context requires otherwise due to express language or necessary implication, the word "comprise" or variations such as "comprises" or "comprising" is used in an inclusive sense, i.e. to specify the presence of the stated features, but not to preclude the presence or addition of further features in various embodiments of the invention.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

An embodiment exemplified for any aspect of the invention is applicable to any other aspect of the invention. In other words, any embodiment exemplified for any aspect of the invention is not to be limited only to that particular aspect of the invention.

EXAMPLES

The invention is now further described in detail by reference to the following example. The example is provided for purposes of illustration only, and is not intended to be limiting unless otherwise specified. Thus, the invention encompasses any and all variations which become evident as a result of the teaching provided herein.

Example 1

Perfusion Apparatus

In one example, the perfusion solution is made by combining a first and second solution in intravenous drip style bags.

Preferably, the perfusion solution should be used within approximately 24 hours of combining. Immediately prior to use, 100% oxygen is then bubbled into the bag(s) containing the first and second solutions in a three stage procedure in order to assure that the solutions are oxygenated.

Figure 3:
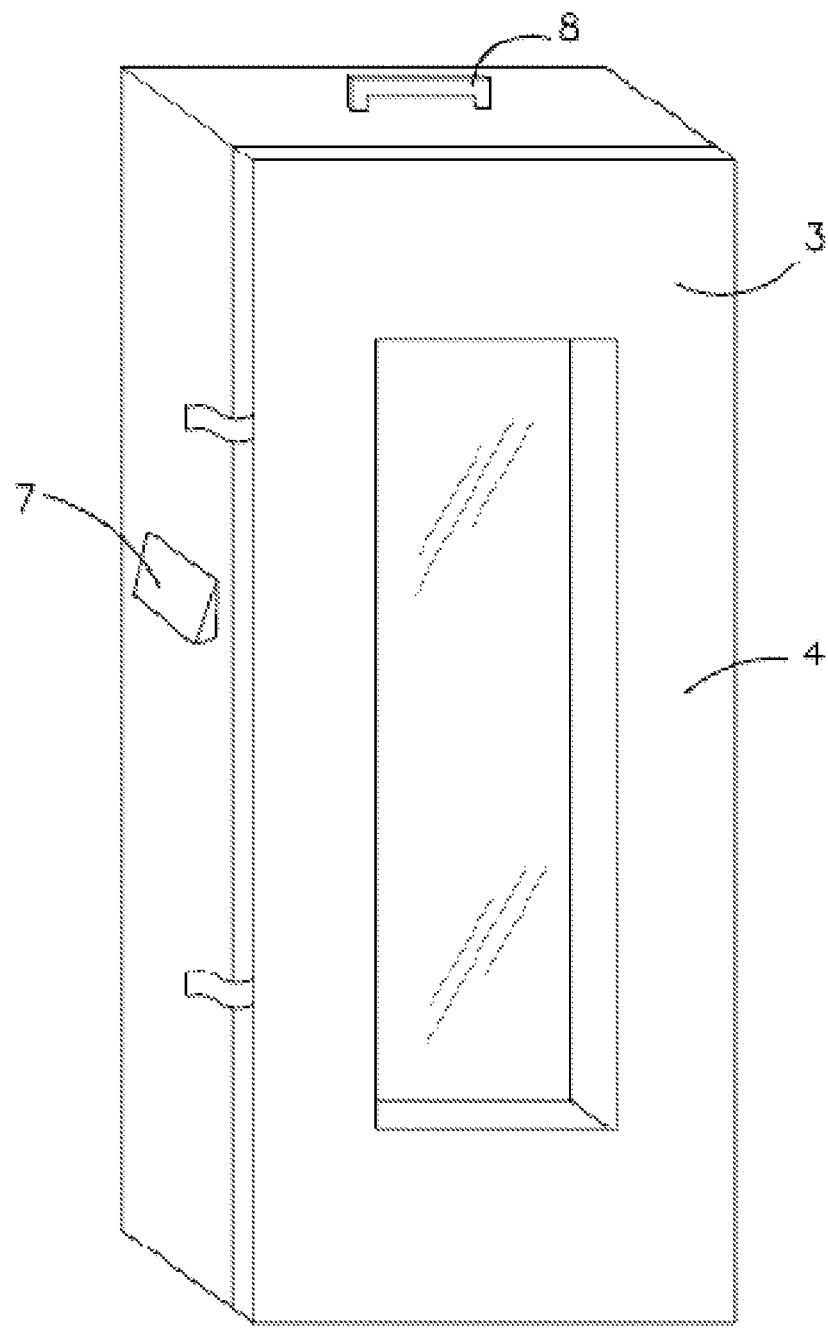
FIG. 3 is a perspective view illustrating a cabinet to house a perfusion composition delivery line assembly attached to a donor heart.
Figure 4:
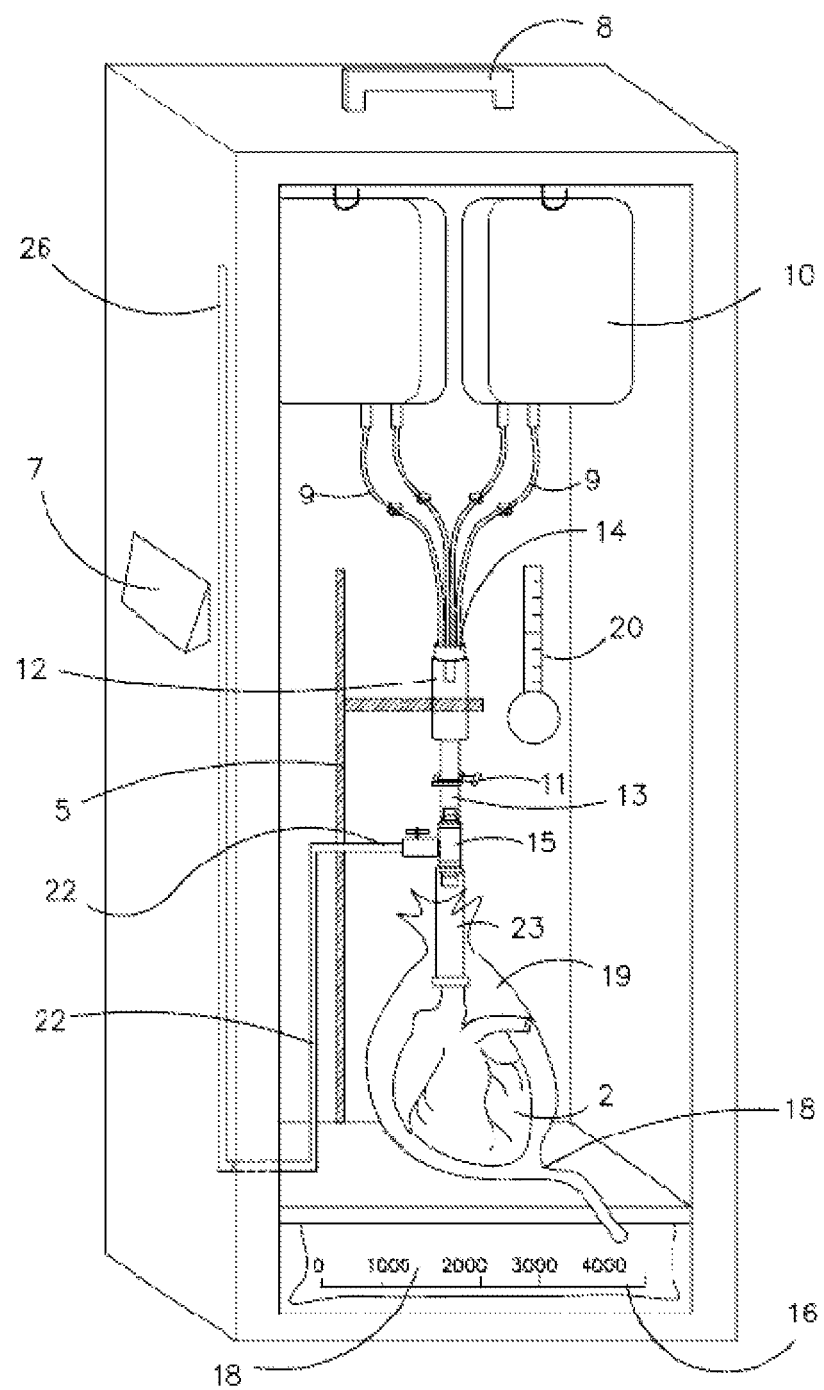
FIG. 4 is a perspective view of the cabinet of FIG. 3 containing the assembly coupled to the donor heart with the door of the cabinet removed.
Figure 5:
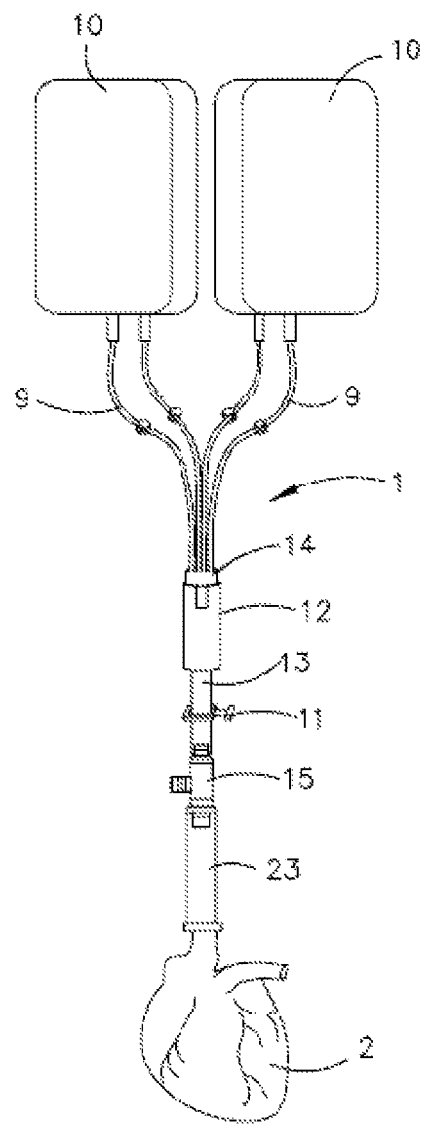
FIG. 5 is a detailed view of the delivery line assembly coupled to the donor heart.

As shown in FIGS. 3, 4 and 5, a multiple of bags 10, the number depending on the length of the perfusion time required, are hung in an insulated enclosure 3 forming part of a micro-perfusion drip apparatus 1. The enclosure 3 is a self standing rectangular cabinet with a hinged glass door 4 at the front. Carry handles 7, 8 are located at the sides and on the top of the cabinet. The cabinet is manufactured in insulated plastics often used in portable fridges and coolers. The insulated enclosure 3 is maintained at a temperature of between 4° C. and 10° C. by use of ice bags (not shown). The solution bags 10 are attached to the top of the enclosure and a stand 5 is used to support the heart 2 so that it is suspended within a plastics bag 19.

The bags 10 are connected by drip lines 9 to a common manifold 14 which exits into a drip chamber 12. The outlet of the drip chamber 12 is coupled to a length of soft plastics tubing which is in turn coupled to a three way connector 15 with a tap. A flow regulator in the form of an adjustable gate clamp 11 is positioned on the soft plastics connector 13. The exit of the three way connector 15 is coupled to an aortic cannula 23 which is securely fitted inside the aorta of the heart 2. The cannula is held within the aorta by appropriate clamps (not shown).

It is also important that the aortic valve of the heart is closed during the perfusion. The solution flows through the coronary arteries, coronary sinus, right atrium, to drop into the bag 19 and then escape into a waste collection or effluent bag 16, located in the base of the enclosure 3. The fluid is collected and not reused. It should be noted that heart 2 is hung by gravity within the plastics bag 19 without support. The solution 18 within the base of the plastics bag 19 ensures that the heart is in a moist environment to prevent drying out. It is important that the heart does not float in the fluid 18.

The angled exit of the three way connector is coupled to a pressure line 22 near the cannula 23 to provide measure of the pressure caused by the flow rate of the solution. Pressure line 22 provides important pressure feedback. The pressure line 22 is coupled to a water manometer 26 attained to the outside of the enclosure. Alternatively, the manometer can be located within the enclosure or on the glass door of the enclosure. Reading of pressure is useful for two reasons: 1) too much pressure can lead to oedema and 2) an easy check to determine whether the aortic valve is closed is to briefly increase the flow rate and the pressure should increase. Regular pressure tests are conducted where the perfusion flow rate is temporarily increased. If the aortic valve is competent, the aortic lost pressure will rise accordingly. If the pressure does not rise, this indicates aortic incompetence. This is rectified by pressurisation of the valve achieved by increasing the flow and ensuring that the heart is positioned correctly to ensure the valve is closed.

The heart 2 is suspended by the aortic cannula 23 at a temperature of between 4 and 10° C. A temperature gauge is positioned to be visible within the enclosure. In this example the heart is perfused with the solution for four hours at a flow of 20 mL/min, during which time the myocardial temperature remained between 5 and 10° C. and the aortic root pressure was between 4-8 mm Hg.

The perfusion apparatus described with reference to FIGS. 3 to 5 provides a very simple and effective portable device. It is designed to be light and easily transportable and is considered to be particularly reliable. There are no moving parts, no need for batteries or power sources, pumps, gas cylinders and refrigeration devices. The apparatus by controlling the flow rate and through the use of a gravity feed at controlled temperatures ensures that the heart is continually perfused during transportation before transplantation. The apparatus is designed to be robust to resist damage during transport. Finally the apparatus has been designed so that it can be managed by a non-expert without the need for a highly skilled technician to ensure efficient operation.

Example 2

12 Hour Preservation of Normal Hearts

Traditionally, preservation of donor hearts for transplantation has been performed using cold storage, which provides satisfactory protection of up to 4 hours after removal from standard brain dead patients. Currently, due to the shortage of donors, surgeons are increasingly accepting hearts that have a prolonged ischemic time prior to transplantation, along with marginal donors and DCD donors.

In the first case, Greyhounds were anesthetized and the heart removed after arrest with St. Thomas's potassium cardioplegia. Greyhound hearts have a structure, weight and composition very similar to human hearts. The hearts were allocated to 12 hour of either perfusion (n=5) or ice storage (n=4). Perfusion hearts received cold crystalloid gravity-feed microperfusion (20 mL/min, 6 mmHg, 4-10° C.) with the perfusion composition of the invention. Cold storage hearts were preserved for 12 hours in ice as in conventional clinical practice, which is known to add to the ischemic damage suffered by the heart after removal, especially those hearts that are donated after cardiac arrest. The sets of hearts were then transferred to a blood perfused working heart apparatus for 2 hours of reperfusion followed by final assessment. Five non-preserved hearts without ischemia were assessed to provide a reference to normal functioning hearts. FIGS. 7 through 10 detail the test results of the perfused normal hearts versus those kept according to standard cardioplegia practices in ice and those normal hearts used as a control lot. It was determined that the perfusion composition herein disclosed as compared to conventional ice storage allowed for the donor hearts to utilize oxygen during their preservation, which is associated with superior post-preservation pump function, efficiency and lactate metabolism. During perfusion, the perfused hearts consumed oxygen. After preservation compared to cold storage hearts, perfused hearts had higher cardiac output, LV dP/dt max and efficiency, with lower lactate; hemodynamic values were 50% to 80% of non-preserved hearts. In terms of lactate metabolism, it was shown that after perfusion, the hearts were aerobic, consuming lactate while the cold storage hearts were anaerobic, producing harmful lactate.

TABLE 6

Summary of Results of Example 2.

| Measurement | Perfusion (n = 5) Mean ± SEM or Median (IQR) | Cold Storage (n = 7) Mean ± SEM or Median (IQR) | P value |
|---|---|---|---|
| Perfusion pressure | 5.4 ± 0.8 mmHg | — | — |
| $O_2$ consumption | 0.09 ± 0.01 mL/100 g/min | — | — |

TABLE 6-continued

Summary of Results of Example 2.

|  | Perfusion (n = 5) Mean ± SEM or Median (IQR) | Cold Storage (n = 7) Mean ± SEM or Median (IQR) | P value |
|---|---|---|---|
| Cardiac output | 1.24 (1.08-1.33) L/min | 0.28 (0.24-0.46) L/min | 0.007 |
| Cardiac power | 9.64 (9.56-9.96) J/min | 0.09 (0.04-0.43) J/min | 0.007 |
| Efficiency | 0.262 (0.177-0.361) J/mL $O_2$ | 0.011 (0.000-0.74) J/mL $O_2$ | 0.018 |
| Lactate metabolism |  |  |  |
| Following simulated transplant | 1.7 ± 0.2 mM | 4.4 ± 1.5 mM |  |
| Following final assessment | 0.9 ± 0.5 mM (Consumption) | 5.6 ± 1.1 mM (Production) | 0.015 |

Accordingly, this invention as disclosed will extend the time of organ viability during transport, between harvest and transplantation, over currently available methods and solutions. It also presents an organ that is more adapted to reperfusion and thusly more likely to successfully transplant and function in the new body.

Example 3

4 Hour Preservation of DCD Hearts

Animal Preparation

The protocol was approved by the Alfred Medical Research and Education Precinct Animal Ethics Committee in accordance with the Australian code of practice for the care and use of animals for scientific purposes 7th Edition 2004.

Male greyhound dogs were premedicated with intramuscular acetylpromazine (0.1 mg/kg). Anaesthesia was then induced with propofol (6 mg/kg), the dog intubated and mechanically ventilated. Anaesthesia was maintained by inhalation of isofluorane (0.5-2%) as required. A cannula was placed in the right internal jugular vein in order to infuse Ringer's solution, sodium bicarbonate (20 mL/hour) and measure central venous pressure. Intravenous morphine (20 mg) was administered for analgesia. The left femoral artery and vein were cannulated to provide arterial pressure monitoring and another avenue for fluid replacement. It was observed that when the dog was placed in the supine position in readiness for surgery, the blood pressure dropped dramatically and a compensatory tachycardia developed. This phenomenon was caused by left ventricular distortion (as seen on echocardiography) and was managed by infusing intravenous Ringer's solution and placing the animal partly on its side as required to maintain a stable blood pressure. A median sternotomy was performed and the pericardium opened. Lignocaine (50 mg) was administered directly into the pericardium to prevent arrhythmias. The great vessels were isolated, the azygous vein ligated and a baseline epicardial echocardiogram performed.

Heparin (10,000 U) was administered intravenously to allow the exsanguination of blood (600 to 900 mL) from the femoral artery. This blood was required to prime the isolated heart (RIG) apparatus. Arterial pressure and heart rate were monitored carefully as blood was removed. Ringer's solution was used to replace blood volume and intravenous phenylephrine (5-10 mg) was given as required to maintain blood pressure at physiological levels.

Perfusion Group

Figure 11:
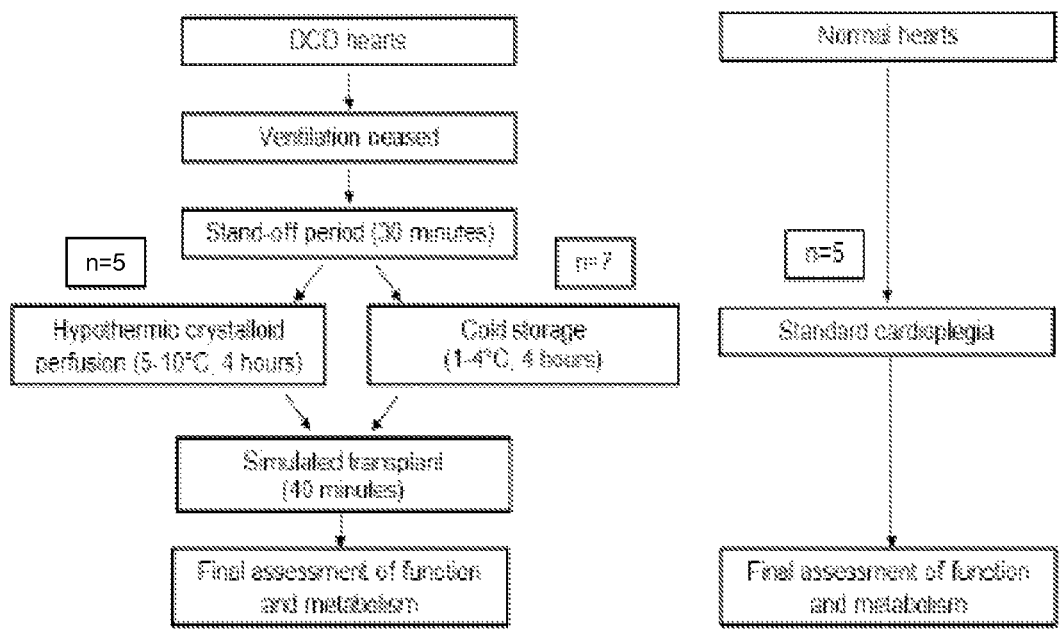
FIG. 11 is a schematic representation of the experimental protocols of Example 3 for comparing the perfusion composition of the invention versus current clinical practice. Left, DCD hearts subjected to hypothermic perfusion preservation or standard preservation for 4 hours. Right, normal hearts.

The experimental protocol for the perfusion group is summarised in FIG. 11.

Induction of Cardiac Arrest by Withdrawal of Ventilation

After blood collection, anaesthesia was deepened and potential respiratory effort depressed by administration of morphine (10 mg) and propofol (200 mg), after which mechanical ventilation was ceased. A strict 30 minute stand-off period was applied following the cessation of ventilation during which time no preservation strategies were employed. This duration was chosen based on the clinical experience from DCD donor lung transplants performed at the Alfred hospital. Mean time between absence of cardiac output and start of cold preservation in human DCD donor lung transplantation at the Alfred hospital was 38.4 minutes if extubation was performed in the intensive care unit (ICU) and 12.7 minutes if extubation occurred in the operating theatre. The transplant unit staff at the Alfred hospital agreed that 30 minutes from cessation of ventilation until the implementation of preservation strategies was appropriate and realistic. Although no preservation techniques were employed, following cessation of ventilation, blood was collected from the femoral vein (200 mL) for the operation of the RIG apparatus and an equal volume of Ringer's solution was infused through the internal jugular vein to avoid a hemodynamic disturbance. Heart rate, electrocardiogram (ECG), arterial pressure and central venous pressure were monitored during the stand-off period. Cardiac arrest occurred 6 to 14 minutes after withdrawing mechanical ventilation. A temperature probe was then inserted into the myocardium.

Two-Part (AMPI) Cardioplegia

Following the 30 minute stand-off period, a two-part cardioplegia was administered over 6 minutes in combination with topical cooling with ice. In total, 1000 mL of crystalloid cardioplegia was infused at a temperature of 4° C. Cardioplegia was vented through the left atrial appendage and the inferior vena cava.

The first part was AMPI Cardioplegia. Five hundred mL of AMPI cardioplegia was administered over 3 minutes. The base for this solution was St. Thomas' Hospital No. 2 cardioplegia with the following additives:

Aspartate (14 mM)
Adenosine (3 mg/L)
Insulin (100 U/L)
Cyclosporine (5 mg/L)
The solution was made acidic (pH of 7.2) by saturation with 20% carbon dioxide The second part was called the 'Recovery Cardioplegia'. Once 500 mL of AMPI cardioplegia was delivered, 500 mL of Recovery Cardioplegia was administered over 3 minutes. The base solution was St. Thomas' Hospital No. 2 cardioplegia saturated with 100% oxygen with the following additives:

Aspartate (14 mM)
Sodium bicarbonate (10 mM)
Cariporide (3.79 mg/L)
The pH of the second or recovery cardioplegic solution was 7.8 at 4° C.

Preservation Conditions

Myocardial temperature was between 5-15° C. following cardioplegia. The heart was then excised and weighed. The pulmonary veins were ligated and an aortic cannula inserted (three eighth-inch diameter PVC tubing with a collar of half-inch diameter PVC tubing (Lovell Surgical, Melbourne)). The left atrial appendage and pulmonary artery were then cannulated with quarter-inch diameter PVC tubing.

The heart was transferred to the perfusion apparatus of the invention (FIGS. 3 to 5). It was designed to be as simple as possible in order to make it portable and convenient. It comprises a polystyrene box with dimensions 92 cm×35 cm×35 cm. The front door has a window to allow monitoring and is closed with Velcro straps. Initially, four 1 liter bags of perfusion composition were suspended from the top of the box, attached to a manifold which leads to a drip chamber. These bags were replaced with new ones as required. The heart was attached distal to this drip chamber and received an infusion of perfusate through the aortic root. The flow rate was controlled by a gate clamp.

The perfusate flowed through the coronary arteries, coronary sinus, right atrium, right ventricle and finally through the main pulmonary artery. Effluent perfusate collected from the pulmonary artery was evidence of nutrient flow that perfused the coronary arteries. In the presence of aortic incompetence effluent would flow past the aortic valve, into the left ventricle and out the left atrium thus bypassing the coronary arteries. The potential problem of aortic incompetence was overcome by conducting regular 'pressure tests' where the perfusion flow rate was temporarily increased. If the aortic valve was competent, the aortic root pressure would rise accordingly. If the pressure did not rise, this indicated aortic incompetence. This was rectified by pressurisation of the valve (achieved by increasing the flow) and ensuring the heart was positioned correctly to ensure the valve was closed.

The heart was suspended by the aortic cannula which was attached to the drip chamber. Ice packs were hung on the walls of the box to maintain a low ambient temperature. There was constant monitoring of pulmonary arterial effluent flow, myocardial temperature (Shiley Inc., California), temperature inside the perfusion apparatus box and aortic pressure (Datex Ohmeda, Melbourne).

Figure 13A:
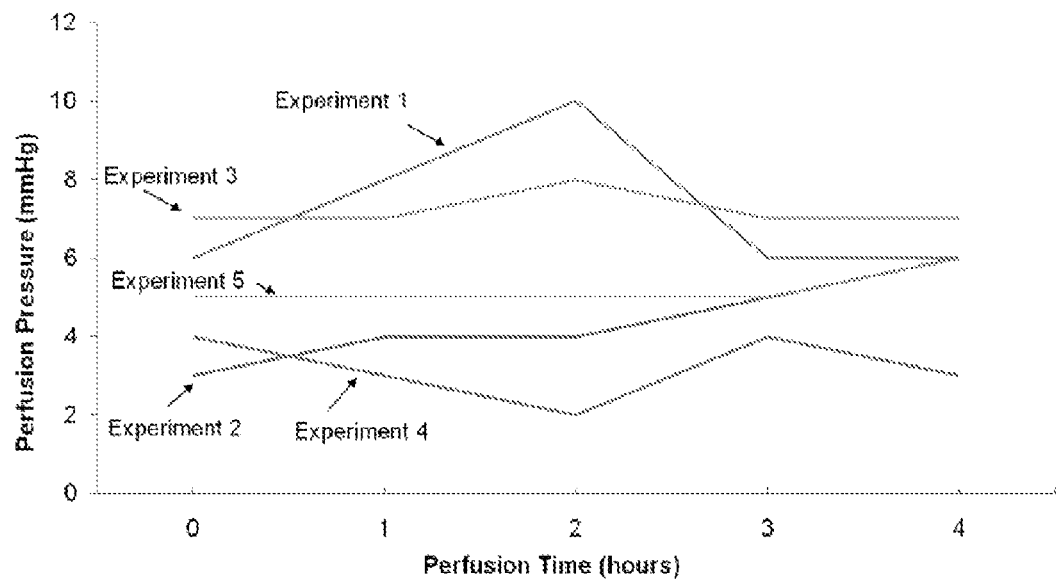
FIG. 13A graphs perfusion pressure of individual experiments during perfusion preservation of DCD hearts perfused for 4 hours according to FIG. 11 and Example 3.
Figure 13B:
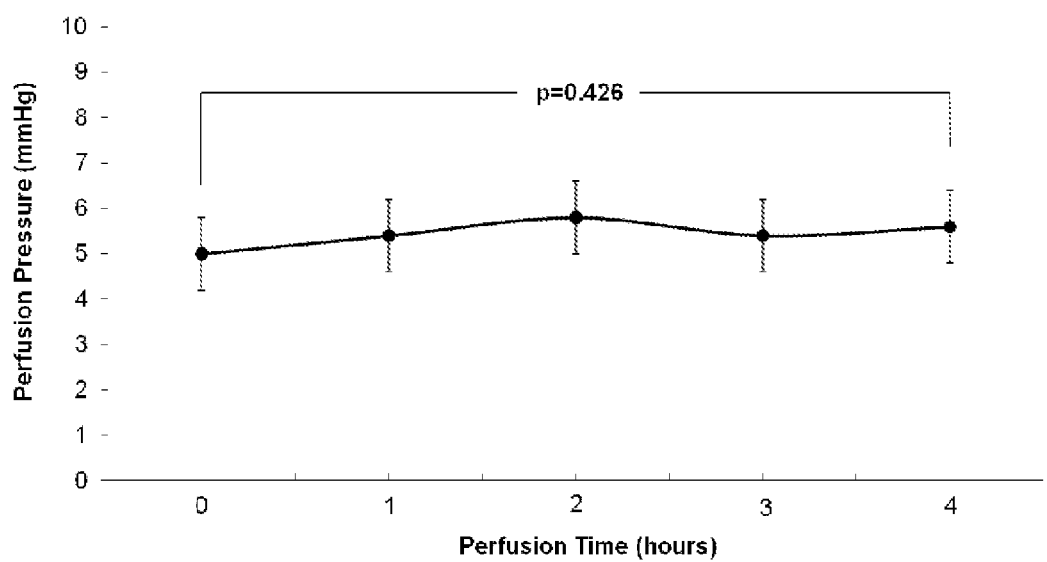
FIG. 13B graphs mean perfusion pressure for all experiments of FIG. 13A.

In total the heart was perfused with perfusion composition for 4 hours at a flow of 20 mL/min, during which time the myocardial temperature remained between 5-10° C. and the mean aortic root pressure between 4-8 mmHg (FIG. 13).

Perfusion Composition

The perfusion composition used in these experiments is defined in Table 5.

Simulated Transplant

Following the 4 hour preservation period the heart was removed from the perfusion apparatus and gradually warmed to room temperature (23° C.) by immersion in warm normal saline. This 40 minute simulated transplant period mimicked the warming experienced by donor hearts during implantation.

Blood Reperfusion

Figure 6:
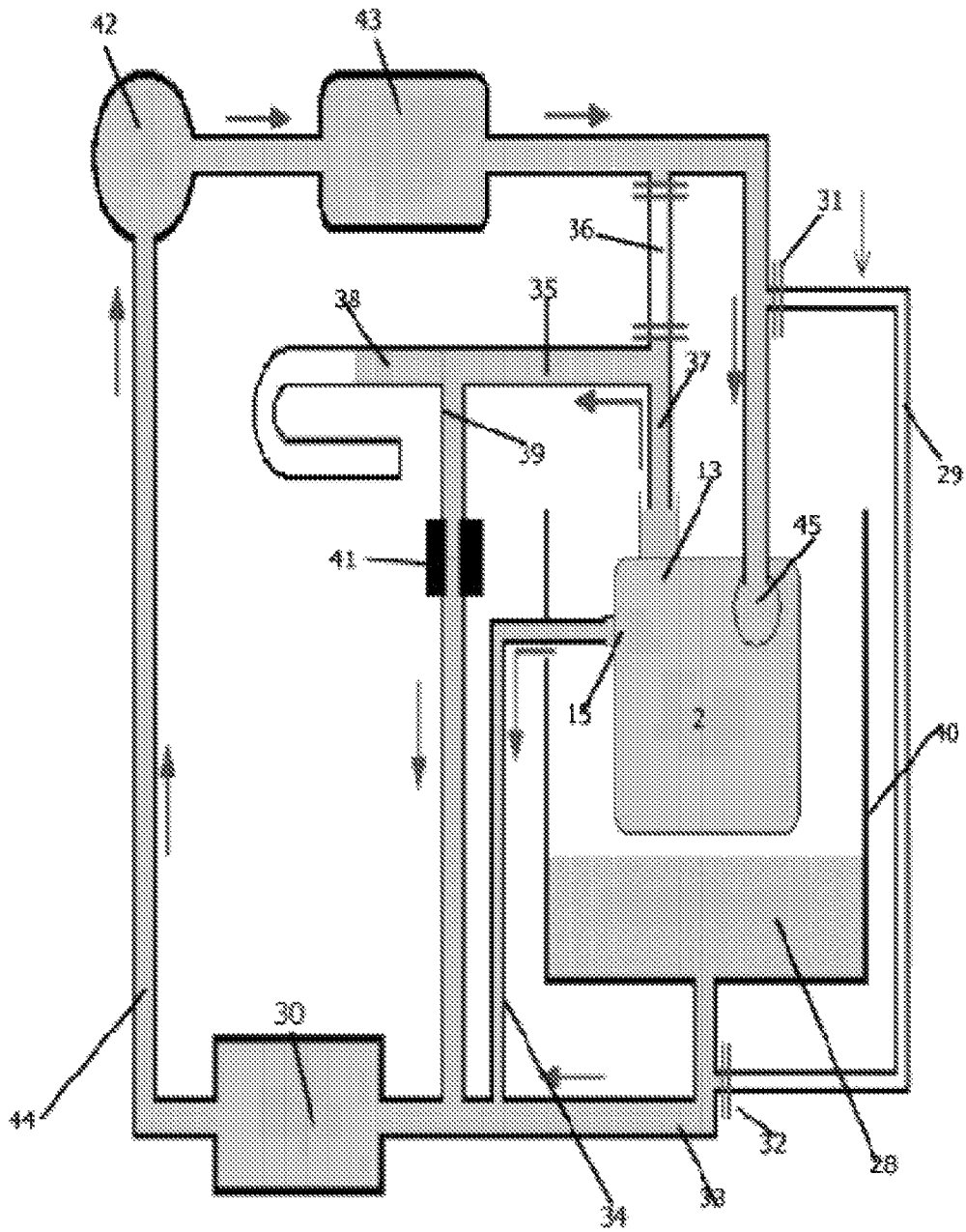
FIG. 6 is a diagrammatic representation of the working heart apparatus used for functional assessment of the heart perfused with the apparatus of FIGS. 3 to 5.
Figure 7:
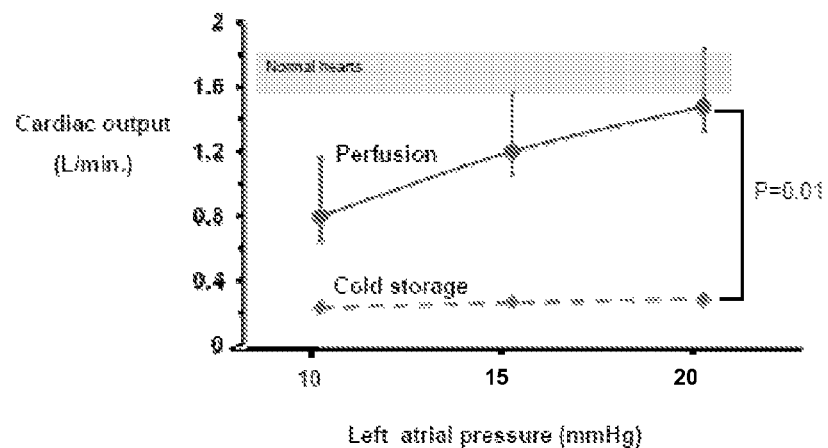
FIG. 7 graphs the effect of left atrial pressure on cardiac output in normal hearts perfused for 12 hours according to Example 2.
Figure 8:
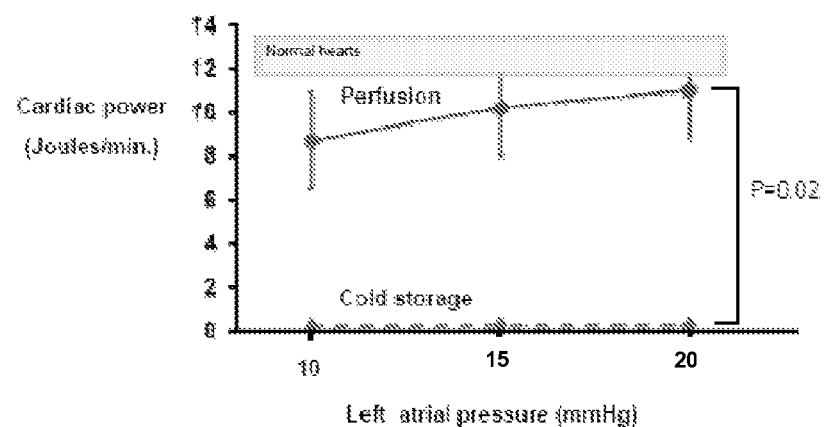
FIG. 8 graphs the effect of left atrial pressure on cardiac power in normal hearts perfused for 12 hours according to Example 2.
Figure 9:
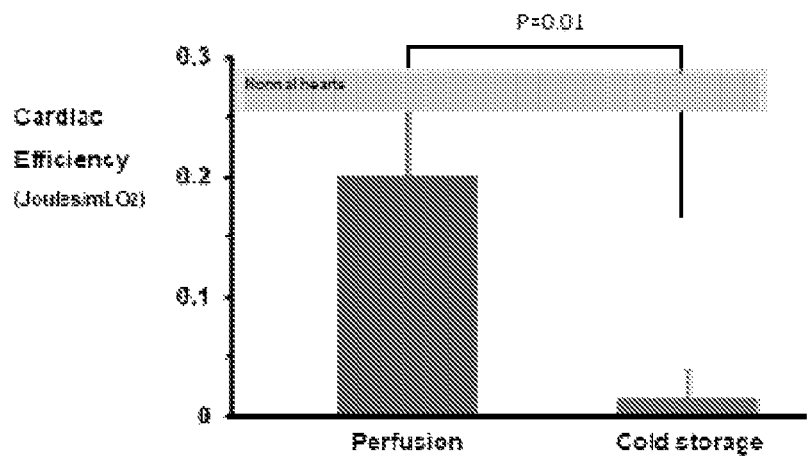
FIG. 9 graphs the effect of cold storage or perfusion on cardiac efficiency in normal hearts perfused for 12 hours according to Example 2.
Figure 10:
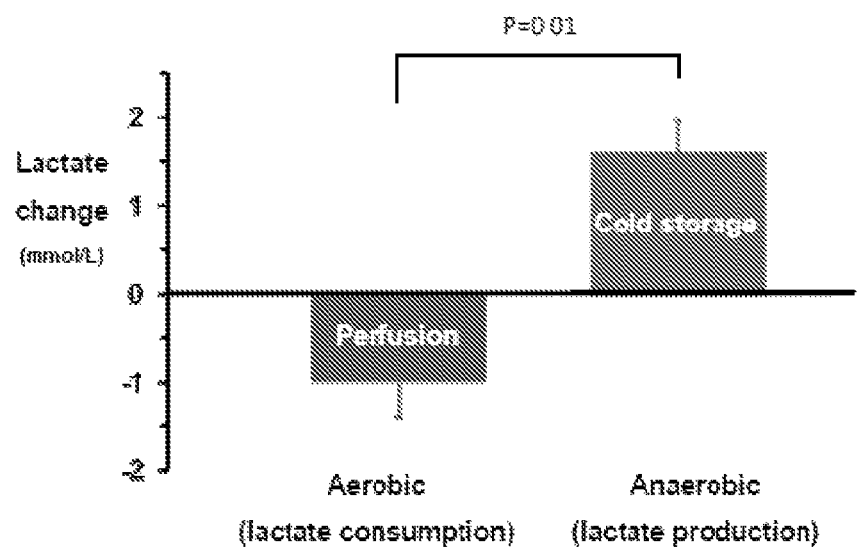
FIG. 10 graphs the effect of cold storage (anaerobic metabolism) or perfusion (aerobic metabolism) on lactate change in normal hearts perfused for 12 hours according to Example 2.

The heart was then connected to the RIG apparatus (FIG. 6) and reperfused with blood for 50 minutes in the non-working mode. The RIG apparatus is a modified extracorporeal membrane oxygenation (ECMO) circuit containing a roller pump (COBE cardiovascular, Arvada), membrane oxygenator (Capiox SX18, Terumo, Melbourne), leucocyte filter (Leuko-Guard, Pall, Sydney) and a heater cooler unit (Jostra, N.J.). In the non-working mode, the coronary arteries are perfused through the aortic root and the heart is not required to eject against resistance. In the working mode, the heart is perfused through the left atrium and must eject against an afterload.

The perfusate consisted of whole blood collected from the greyhound. In some experiments, Ringer's solution was added to achieve the 1200 mL required priming volume of the circuit. The blood was leucocyte depleted, temperature controlled and its partial pressure of oxygen and carbon dioxide carefully regulated. The following were added to the blood during circuit priming:

Heparin (1000 IU/1200 mL)
Glucose (2 g/1200 mL)
Insulin (50 U/1200 mL)
Aspartate (14 mmol/1200 mL)
Sodium bicarbonate (20 mmol/1200 mL)

A controlled reperfusion strategy was employed in an attempt to minimise reperfusion injury and to optimise functional recovery (Table 7). Hearts were initially reperfused under the following conditions:

Aortic pressure of 20-25 mmHg
Blood temperature of 20° C.
Blood oxygenated with a 20% oxygen:air mixture
Carbon dioxide flow of approximately 150 mL/min in order to render the blood acidic (pH 7.30-7.35) and partial pressure of carbon dioxide high (45-60 mmHg)
The first 100-200 mL of perfusate was discarded to ensure that cardioplegia remaining in the heart from the preservation period was not added to the circuit After 5 minutes of reperfusion, the aortic root pressure was increased to 30 mmHg, heater cooler unit temperature increased to 30° C. and the oxygen:air ratio increased to 50%. Then at 15 minutes of reperfusion, the aortic root pressure was increased to 35 mmHg, heater cooler unit temperature increased to 39° C. and the carbon dioxide flow adjusted in order to achieve a partial pressure of 40 mmHg. Finally, at 20 minutes of reperfusion, the aortic root pressure was increased to 60 mmHg.

TABLE 7

Controlled reperfusion protocol.

| Reperfusion time (min) | Aortic root pressure (mmHg) | Heater cooler unit temperature (° C.) | Oxygen:air mixture (%) | $CO_2$ (mL/min) |
|---|---|---|---|---|
| 0 | 20-25 | 20 | 20 | 150 |
| 5 | 30 | 30 | 50 | 150 |
| 15 | 35 | 39 | 50 | Adjusted to achieve $pCO_2$ of 40 mmHg |
| 20 | 60 | 39 | 50 | |

The hearts were gradually warmed and electrically defibrillated when the myocardium reached 36-37° C. All hearts received lignocaine (1 mg/kg) to prevent arrhythmias. Amiodarone (2.5 mg/kg) was administered if hearts did not achieve a stable rhythm. Electrical pacing was introduced if the heart rate dropped below 90 beats per minute. The blood perfusate composition was carefully controlled with particular attention given to pH, partial pressure of oxygen, partial pressure of carbon dioxide, base excess and concentration of potassium. Inotropes were not administered.

After 50 minutes of reperfusion the RIG apparatus was switched to working mode in order to conduct a final assessment of function and metabolism. To conclude the experiment the whole heart was perfused with 10% neutral buffered formalin through the aortic root.

Standard Preservation Group

The experimental protocol for the standard preservation group is summarised in FIG. 11. Standard preservation data are derived in part from our historical data.

Induction of cardiac arrest by withdrawal of ventilation was conducted as for the perfusion group.

Cardioplegia

Following the 30 minute stand-off period, the aorta was cross clamped and 1000 mL of cardioplegia infused into the aortic root via a 12-gauge intravenous cannula. The cardioplegic solution used in this group was the standard one used in human heart transplantation at the Alfred Hospital. This consisted of St. Thomas' Hospital No. 2 cardioplegia saturated with 100% oxygen with the following additives:
Aspartate (14 mM)
Sodium bicarbonate (10 mM)
The cardioplegia was administered over 6 minutes at 4° C. and the effluent discarded. The heart also received topical cooling with ice.

Preservation Conditions

Myocardial temperature was between 5-15° C. after cardioplegia. The heart was then excised and weighed. The pulmonary veins were surgically ligated, a cannula inserted into the aorta and a myocardial temperature probe positioned in the myocardium. The heart was secured within a watertight bag filled with cold saline (4° C.) which was subsequently placed in an ice box and surrounded by ice. The myocardial temperature gradually decreased in the early stages of preservation, and remained between 1-4° C. for the majority of storage. In total the heart was cold stored for 4 hours.

At the conclusion of the preservation period the left atrial appendage and pulmonary artery were cannulated with quarter-inch diameter PVC tubing.

Simulated transplant was conducted as for the perfusion group.

Blood reperfusion was conducted as for the perfusion group.

Normal Heart Group

A normal heart group was included to provide a reference point for the previously described experimental groups. There was no DCD process or storage period in this group (FIG. 11).

Cardioplegia

After arterial blood collection the aorta was cross-clamped and 1000 mL of cold (4° C.) cardioplegia administered through the aortic root. The standard Alfred Hospital cardioplegia was used in this group (St. Thomas' Hospital No. 2 solution with 14 mM aspartate, 10 mM sodium bicarbonate and saturated with oxygen). Topical cooling was achieved with ice. Ventilation was ceased following cardiac arrest. Myocardial temperature was between 5-15° C. at arrest. Blood was collected from the jugular and femoral veins for the RIG apparatus (1000 to 1500 mL). Hearts were immediately excised and weighed. The pulmonary veins were surgically closed and the aortic, left atrial and pulmonary arterial cannulas inserted.

Blood reperfusion was conducted as for the perfusion group.

Assessment of Function, Metabolism and Histology

Figure 12:
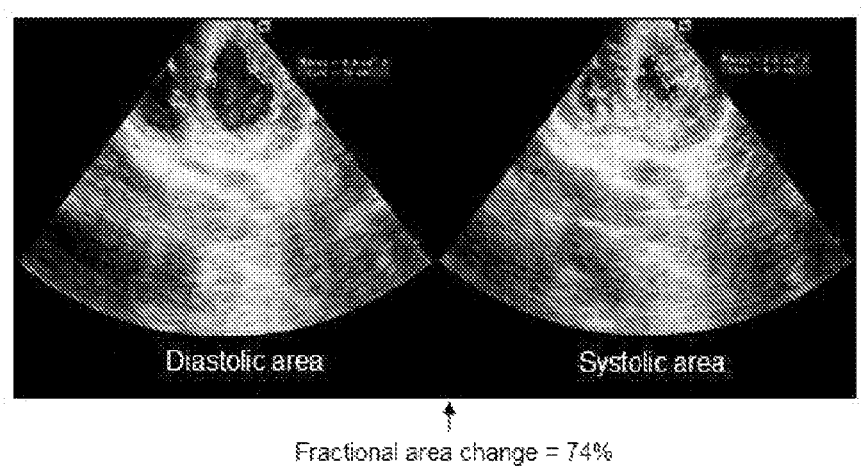
FIG. 12 is an echocardiographic view used for calculation of fractional area change.

Echocardiography (ACUSON Cypress cardiovascular system, Siemens Medical Solutions, Malvern USA) was used to assess baseline heart function. Two dimensional, short axis images were obtained at the level of the tips of the papillary muscles and the area of the left ventricular cavity measured in both systole and diastole. These values were used to calculate the fractional area change (FAC) (FIG. 12). Hearts with less than 25% FAC were excluded from the study. The formula used for FAC was:

$$\text{Fractional area change (\%)}=(\text{Diastolic area}-\text{Systolic area})/\text{Diastolic area}$$

The perfusion group was assessed for oxygen consumption during perfusion. This was achieved by measuring the oxygen content in the perfusate and effluent. In order to bring values into the measurable range, samples were diluted. 1 mL samples of both perfusate and effluent were each mixed with 1 mL of desaturated perfusate (oxygen-free). These 2 mL samples of diluted perfusate and diluted effluent were then analysed in a blood gas analyser at 37° C. (Osmetech OPTI, Osmetech Critical Care, London). This was performed at low, medium and high flows in order to investigate the relationship between coronary perfusate flow and oxygen consumption. Following, are the formulae used to calculate oxygen consumption of the heart.

$$[O_2]=(pO_2 \text{ of diluted perfusate or effluent} \times 0.0289 \times 2 \text{ mL})-(pO_2 \text{ of desaturated perfusate} \times 0.0289 \times 1 \text{ mL}) \quad 1.$$

$[O_2]$=oxygen content of perfusate or effluent (mL $O_2$/mL), $pO_2$=partial pressure of oxygen (mmHg), 0.0289 is the solubility value for oxygen at 37° C.

$$MVO_2=(CPF \times ([PO_2]-[EO_2]))/(\text{Heart weight}/100) \quad 2.$$

$MVO_2$=myocardial oxygen consumption (mL $O_2$/100 g/min), CPF=coronary perfusate flow (mL/min), $[PO_2]$=oxygen content of perfusate (mL $O_2$/mL), $[EO_2]$=oxygen content of effluent (mL O2/mL), Heart weight (g)

Perfused hearts were also monitored for lactate production during perfusion. Samples of effluent for lactate measurement were obtained at the beginning of perfusion and every two hours thereafter. Lactate production was calculated as follows:

$$\text{Lactate production}=\text{Lactate level} \times CPF$$

Lactate production (mmol/min), Lactate level (mmol/L), CPF=coronary perfusion flow (L/min)

Perfusion pressure was recorded at regular intervals throughout preservation.

All three groups were assessed on the RIG apparatus in working mode with the heart pumping against an afterload. Left atrial, left ventricular and aortic root pressures were continuously measured by pressure transducers (Edwards Lifesciences, California) and recorded by the PowerLab system (ADInstruments, Sydney).

Starling function curves were generated by adjusting pump flow to a low left atrial pressure (e.g. 5 mmHg) and gradually increasing flow to assess the heart's ability to respond to increasing preload. This technique allowed the construction of function curves of cardiac power (work performed by the heart per minute) versus left atrial pressure (LAP) and cardiac output (measured by pump flow) versus LAP. The formula for cardiac power is:

$$\text{Cardiac Power}=0.0133 \times CO \times (MAP-LAP)$$

Cardiac Power (Joules/minute), CO=cardiac output (dL/min), MAP=mean arterial pressure (mmHg), LAP=left atrial pressure (mmHg), 0.0133 is the conversion factor between mmHg dL and joules Left ventricular pressure (LVP) was measured through an apical cannula positioned in the left ventricular lumen, which was connected to a high fidelity manometer line and pressure transducer. This enabled the calculation of the maximum rate of change of left ventricular pressure (LV+dp/dt).

Myocardial oxygen efficiency was measured by the number of joules (amount of work) produced by the heart per unit of oxygen consumed. Hearts were placed in working mode at an LAP of 10 mmHg to assess efficiency. Oxygen consumption was calculated by analysis of arterial (aortic line) and venous (pulmonary arterial line) blood samples by a blood gas analyser (Osmetech OPTI, Osmetech Critical Care, London). First, the oxygen content of the arterial and venous samples was determined, then the Fick Principle was used to calculate the oxygen consumption of the heart. Finally, the myocardial oxygen efficiency was determined using the cardiac power and the oxygen consumption.

$$[O_2]=[Hb]\times 1.34\times(SaO_2/100)+(PO_2\times 0.003) \quad 1.$$

$[O_2]$=oxygen content (mL $O_2$/dL), [Hb]=haemoglobin concentration (g/dL), $SaO_2$=oxygen saturation (%), $PO_2$=partial pressure of oxygen (mmHg), 1.34 mL is the amount of oxygen each gram of haemoglobin can bind, 0.003 is the constant for the dissolved oxygen in plasma $$O_2 \text{ consumption}=CBF\times([AO_2]-[VO_2]) \quad 2.$$

$O_2$ consumption (mL $O_2$/min), CBF=coronary blood flow (dL/min), $[AO_2]$=oxygen content of arterial blood (mL $O_2$/dL), $[VO_2]$=oxygen content of venous blood (mL $O_2$/dL)

$$\text{Myocardial oxygen efficiency}=\text{Cardiac Power}/O_2 \text{ consumption} \quad 3.$$

Myocardial oxygen efficiency (J/mL $O_2$), Cardiac Power (J/min), $O_2$ consumption (mL $O_2$/min)

In the perfusion technique and standard preservation groups, blood samples were taken from the RIG apparatus to determine lactate levels at different stages of the experiment. A blood sample was taken moments before hearts were attached to the RIG apparatus to determine a baseline lactate level in the blood perfusate. Samples were then obtained following simulated transplant 15 minutes after the heart was attached to the RIG and then following functional assessment in working mode. All lactate analysis was performed by the clinical biochemistry department at the Alfred Hospital.

Power calculations were based on historical data. The maximum rate of change of left ventricular pressure (LV+dp/dt) was the parameter chosen to perform these calculations. The mean difference in LV+dp/dt between perfusion and cold storage groups was 785 mmHg/s and the common standard deviation was 466 mmHg/s. A statistical power of 80% and a significance level of 0.05 were desired. Thus, the calculated necessary sample size was 6 per group.

A p-value<0.05 was used for statistical significance. Statistical comparisons were made only between the perfusion technique and standard preservation groups. The normal heart group simply provided an indication of the normal range. Data that followed the normal distribution is presented as mean plus/minus standard error of mean (mean±SEM). An independent t-test, paired t-test, one-way analysis of variance (ANOVA) and repeated measures ANOVA were used for statistical comparison. Non-parametric data is expressed as median and inter-quartile range (median(IQR)) and the Mann-Whitney Signed Rank Test was used to determine statistical significance.

Results

A total of 16 male greyhound dogs were used for this study. One perfusion experiment was excluded due to poor baseline fractional area change (FAC) on echocardiography. The baseline characteristics for dogs included for analysis were very similar. Out of the seven standard preservation experiments, one was conducted recently, whilst the other six were historical controls from the unit's previous DCD donor heart project which were subjected to an identical protocol.

TABLE 8

Baseline characteristics of Example 3.

| | Perfusion technique group (n = 5) | Standard preservation group (n = 7) | Normal heart group (n = 3) | p value |
|---|---|---|---|---|
| Dog weight (kg) | 32.0 ± 1.3 | 30.4 ± 0.7 | 30.1 ± 2.1 | 0.510 |
| Baseline fractional area change (%) | 47.2 ± 8.0 | 58.7 ± 7.9 | 45.7 ± 3.0 | 0.447 |
| Time to cardiac arrest (min) | 10.8 ± 1.0 | 8.1 ± 0.9 | — | 0.079 |
| Total ischemic time (min) | 340 ± 5 | 331 ± 5 | — | 0.222 |

Perfusion pressure remained low (generally between 4-8 mmHg) and stable throughout perfusion (FIG. 13). The mean perfusion pressure over all time periods for all experiments was 5.4±0.8 mmHg. The mean increase in perfusion pressure between the beginning and end of perfusion (0.6±0.7 mmHg) was not statistically significant (p=0.426).

Figure 14:
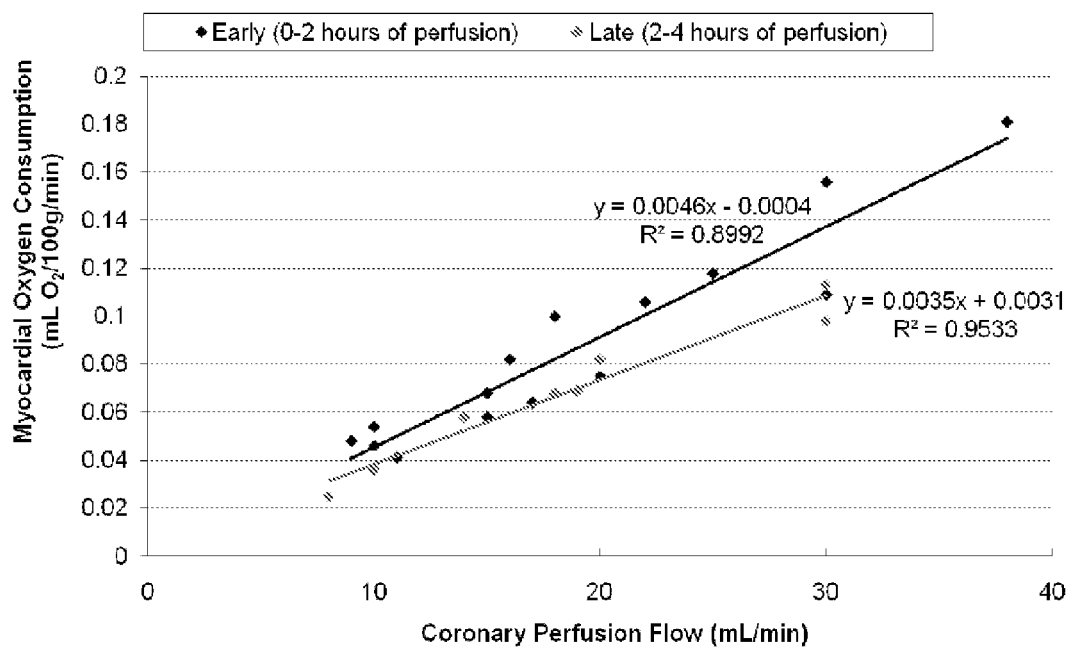
FIG. 14 graphs myocardial oxygen consumption during perfusion against coronary perfusion flow in DCD hearts perfused for 4 hours according to FIG. 11 and Example 3.

Myocardial oxygen consumption increased with coronary perfusion flow. It also showed a trend towards decreasing throughout the perfusion period (FIG. 14). In the early stages of perfusion (between 0 and 2 hours), myocardial oxygen consumption at a flow of 10 mL/min was 0.046 mL $O_2$ per 100 g heart weight per minute (mL $O_2$/100 g/min), 0.092 mL $O_2$/100 g/min at 20 mL/min and 0.138 mL $O_2$/100 g/min at 30 mL/min. At a later time (between 2 and 4 hours of perfusion), myocardial oxygen consumption decreased and at a flow of 10 mL/min was 0.038 mL $O_2$/100 g/min, 0.073 mL $O_2$/100 g/min at 20 mL/min and 0.108 mL $O_2$/100 g/min at 30 mL/min.

Figure 15A:
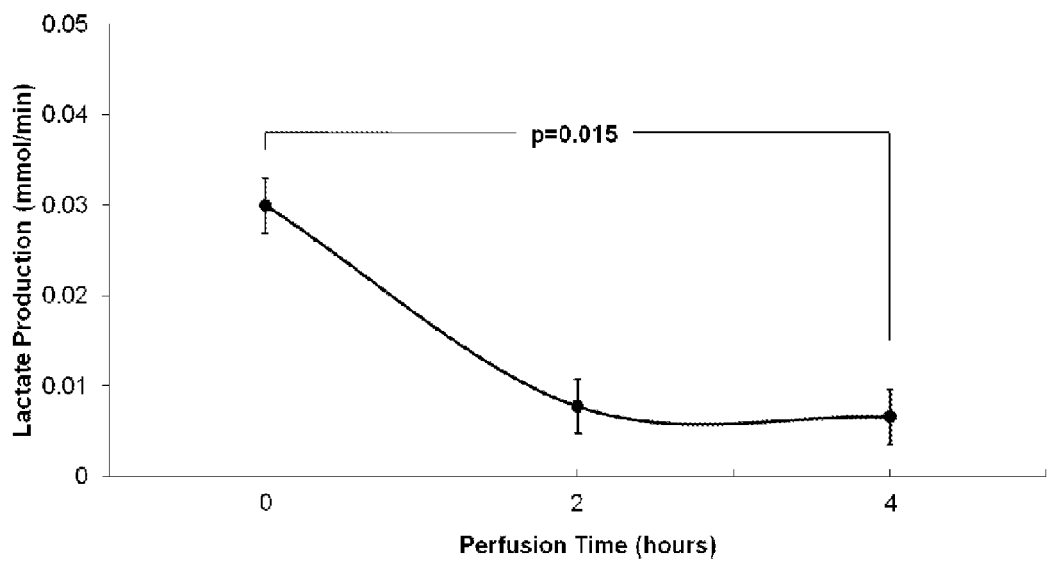
FIG. 15A graphs the effect of perfusion time on lactate production in DCD hearts perfused for 4 hours according to FIG. 11 and Example 3.

Lactate production at the beginning of perfusion was 0.030±0.005 mmol/min, 0.008±0.001 mmol/min at 2 hours of perfusion and 0.007±0.002 mmol/min at the end of perfusion. Lactate production was less at the end of perfusion compared to at the beginning of perfusion (p=0.015) (FIG. 15A).

Figure 15B:
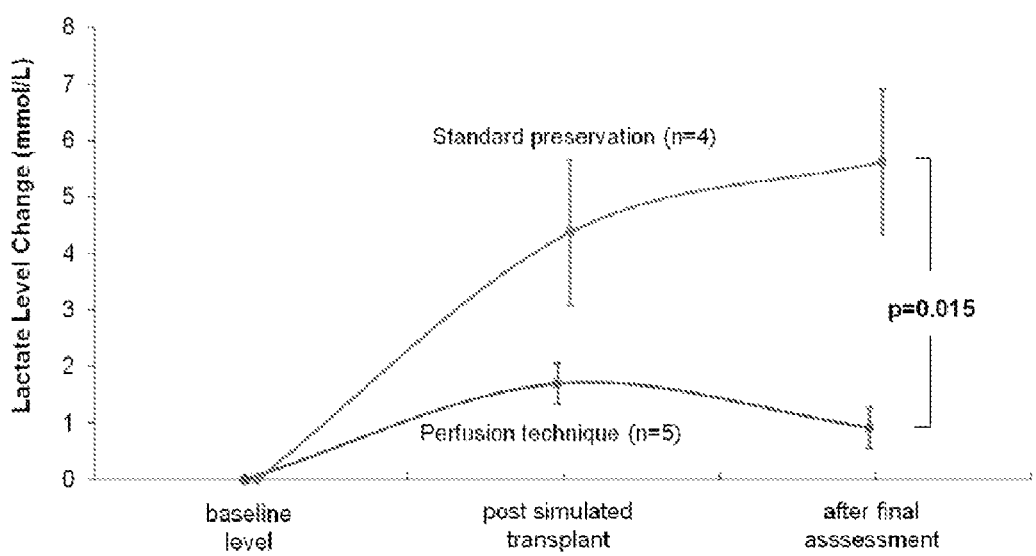
FIG. 15B graphs the lactate level on the RIG apparatus of DCD hearts perfused for 4 hours according to FIG. 11 and Example 3.

Blood samples were obtained from the isolated heart (RIG) apparatus to measure lactate levels (FIG. 15B). The measurements were of the baseline (heart not attached to RIG), following simulated transplant (15 minutes after the heart was attached to RIG), and after final assessment. In the perfusion technique group the change in lactate level post simulated transplant and after final assessment was 1.7±0.2 mmol/L and 0.9±0.5 mmol/L respectively, and in the standard preservation group 4.4±1.5 mmol/L and 5.6±1.1 mmol/L respectively. The standard preservation group had a significantly greater mean lactate level than the perfusion technique group (p=0.015).

Figure 16A:
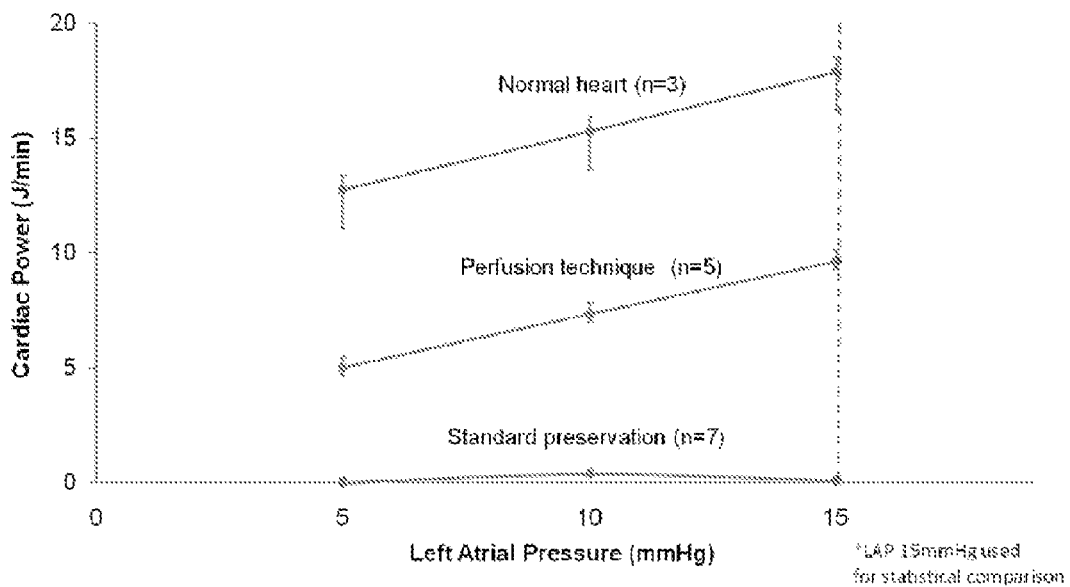
FIG. 16A graphs the effect of left atrial pressure on cardiac power in DCD hearts perfused for 4 hours according to FIG. 11 and Example 3.
Figure 17A:
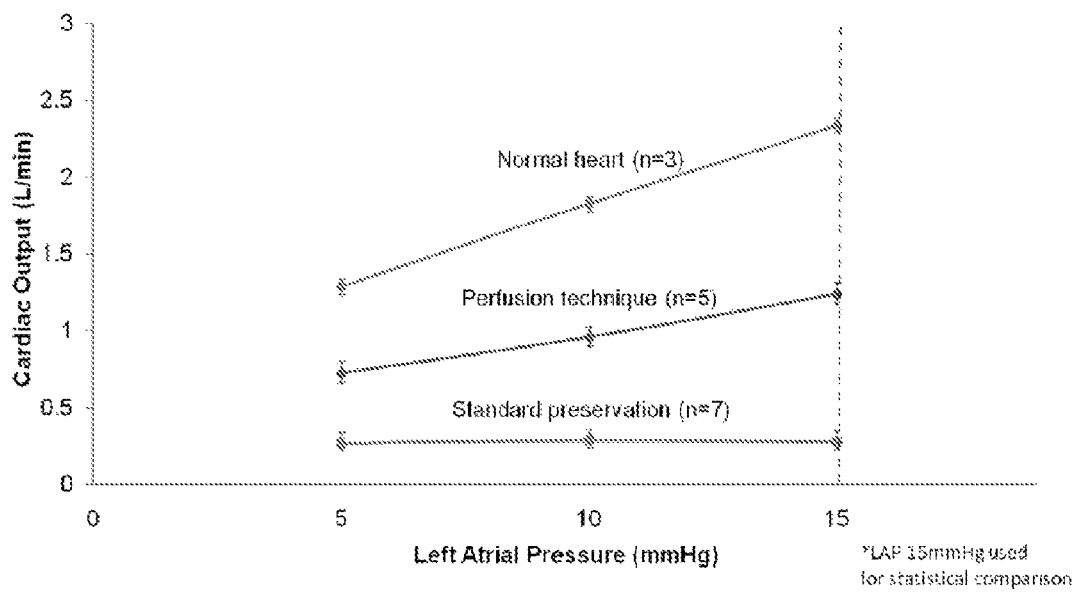
FIG. 17A graphs the effect of left atrial pressure on cardiac output in DCD hearts perfused for 4 hours according to FIG. 11 and Example 3.

Cardiac function was assessed by measuring cardiac power and cardiac output at various left atrial pressures (LAP). The cardiac function curves suggest that the perfusion technique group had superior cardiac power and cardiac output compared to the standard preservation group. Neither group reached the function of the normal heart group (FIGS. 16A, 17A).

Statistical comparisons were conducted for cardiac power, cardiac output and maximum rate of change of left ventricular pressure (LV+dp/dt) at a left atrial pressure of 15 mmHg, the point of maximum cardiac performance.

Figure 16B:
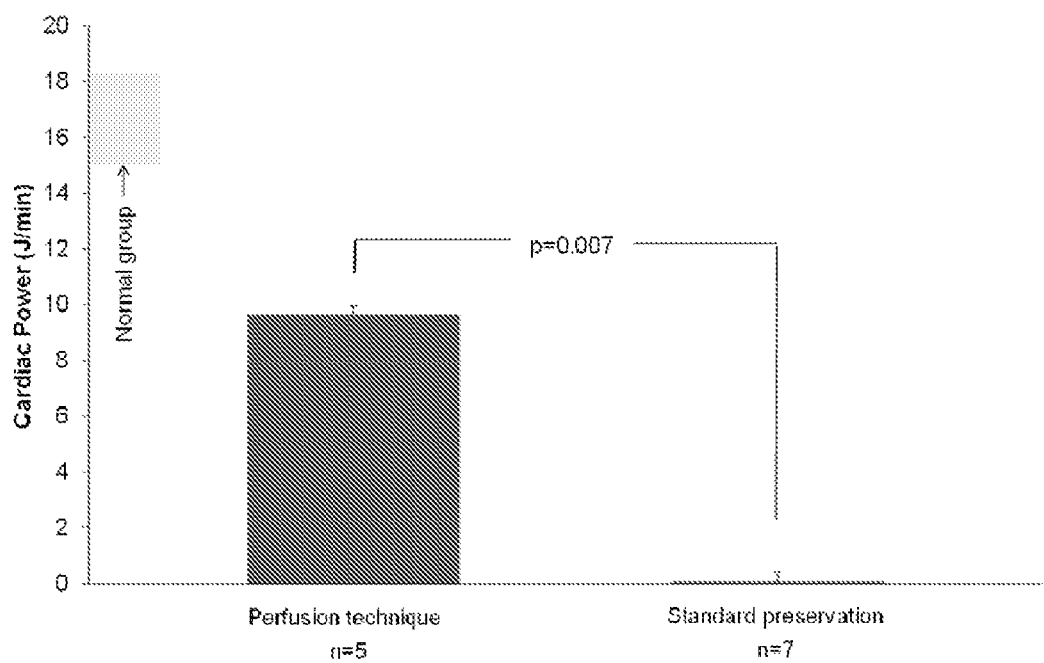
FIG. 16B graphs the effect of 4 hours of standard preservation (cold storage) or perfusion on cardiac power of DCD hearts at 15 mmHg left atrial pressure treated according to FIG. 11 and Example 3.

Cardiac power was significantly greater in the perfusion technique group 9.6 (9.56-9.96) J/min, compared to the standard preservation group 0.09 (0.04-0.43) J/min (p=0.007). The normal hearts achieved a cardiac power of 17.90 (15.01-18.23) J/min (FIG. 16B).

Figure 17B:
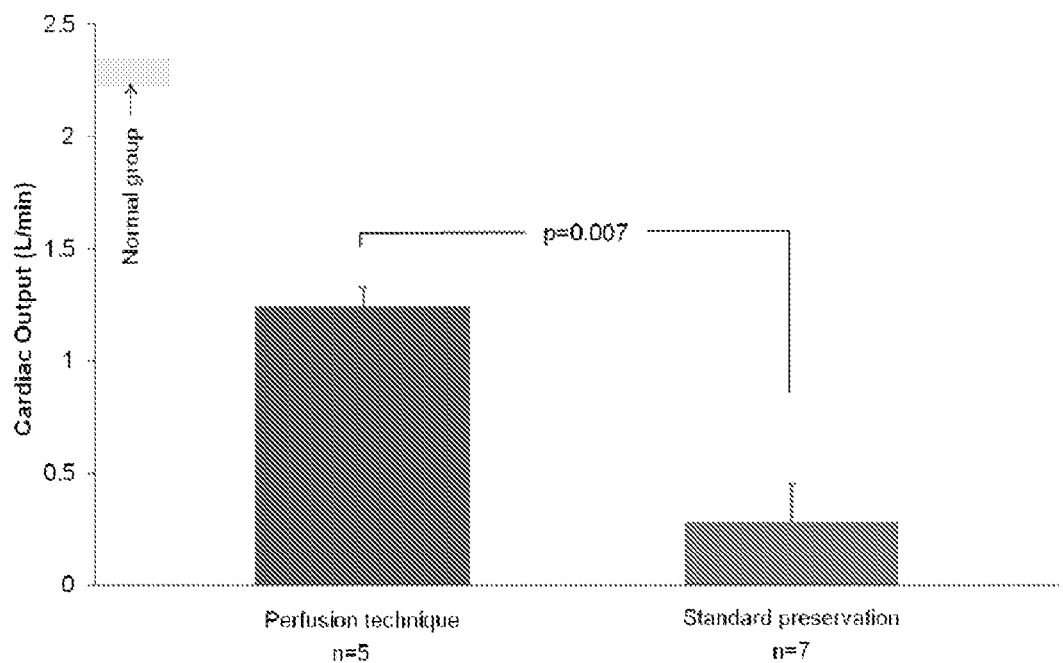
FIG. 17B graphs the effect of 4 hours of standard preservation (cold storage) or perfusion on cardiac output of DCD hearts at 15 mmHg left atrial pressure treated according to FIG. 11 and Example 3.

Similarly the perfusion technique group had a significantly greater cardiac output 1.24 (1.08-1.33) L/min, compared to the standard preservation group 0.28 (0.24-0.46) L/min (p=0.007). Cardiac output was 2.34 (2.23-2.35) L/min in the normal heart group (FIG. 17B).

Figure 18:
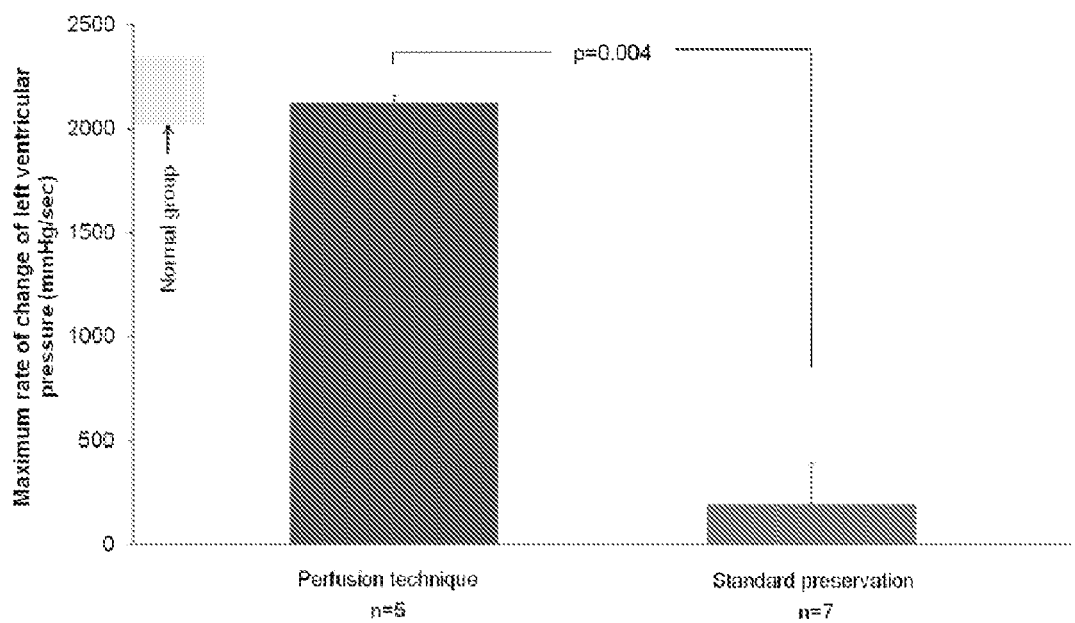
FIG. 18 graphs the effect of 4 hours of standard preservation (cold storage) or perfusion on maximum rate of change of left ventricular pressure of DCD hearts at 15 mmHg left atrial pressure treated according to FIG. 11 and Example 3.

LV+dp/dt was also significantly greater in the perfusion technique group 2127 (2057-2162) mmHg/sec, compared to the standard preservation group 190 (139-395) mmHg/sec (p=0.004). The normal heart group had a LV+dp/dt of 2319 (2015-2344) mmHg/sec (FIG. 18).

Figure 19:
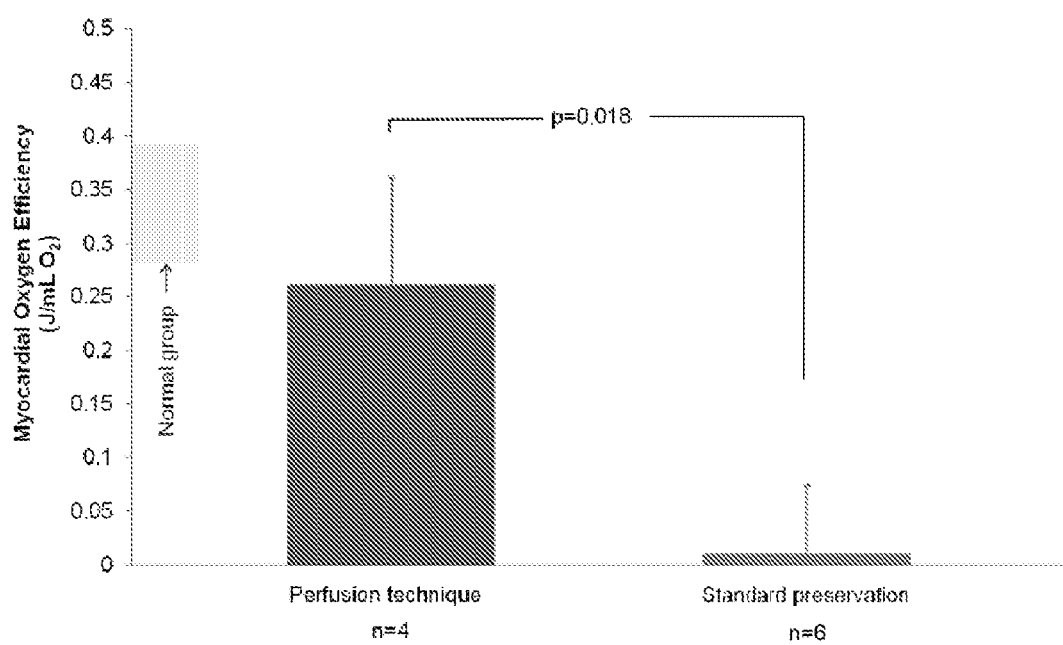
FIG. 19 graphs the effect of 4 hours of standard preservation (cold storage) or perfusion on myocardial oxygen efficiency of DCD hearts at 10 mmHg left atrial pressure treated according to FIG. 11 and Example 3.

Myocardial oxygen efficiency was calculated at a LAP of 10 mmHg for statistical analysis. The perfusion technique group had a significantly greater myocardial oxygen efficiency of 0.262 (0.177-0.361) J/mL $O_2$ compared to the standard preservation group's 0.011 (0.000-0.074) J/mL $O_2$ (p=0.018). The efficiency of the normal heart group was 0.334 (0.282-0.393) J/mL $O_2$ (FIG. 19).

TABLE 9

Summary of results for Example 3.

| Parameter | Perfusion technique (n = 5) (median (IQR)) | Standard preservation (n = 7) (median (IQR)) | p value |
|---|---|---|---|
| Oxygen consumption during perfusion (mL/100 g/min) (mean) | Early: 0.092 Late: 0.073 | — | — |
| Perfusion pressure (mmHg) (mean ± SEM) | 5.4 ± 0.8 | — | — |
| Lactate production during perfusion (mmol/min) (mean ± SEM) | Beginning: 0.030 ± 0.005 End: 0.007 ± 0.002 | — | — |
| Cardiac power (J/min) | 9.64(9.56-9.96) | 0.09(0.04-0.43) | 0.007 |
| Cardiac output (L/min) | 1.24(1.08-1.33) | 0.28(0.24-0.46) | 0.007 |
| Maximum rate of change of left ventricular pressure (mmHg/sec) | 2127(2057-2162) | 190(139-395) | 0.004 |
| Myocardial oxygen efficiency (J/mL $O_2$) | 0.262(0.177-0.361) | 0.011(0.000-0.074) | 0.018 |
| Lactate level change (mmol/L) (mean ± SEM) | | | |
| Following simulated transplant | 1.7 ± 0.2 | 4.4 ± 1.5 | 0.015 |
| Post final assessment | 0.9 ± 0.5 | 5.6 ± 1.1 | |

Discussion

During hypothermic perfusion preservation, the donation after cardiac death (DCD) donor heart demonstrated substantial oxygen consumption. Oxygen consumption and lactate production decreased throughout perfusion. Perfusion pressure generally remained low and there was no increase in pressure between the beginning and end of perfusion. Compared to the standard preservation group, the perfusion technique group showed significantly superior recovery in terms of cardiac power, cardiac output, maximum rate of change of left ventricular pressure, myocardial oxygen efficiency and lactate metabolism. The perfusion technique group did not achieve the function of the normal heart group in terms of cardiac power and cardiac output, but was comparable in maximum rate of change of left ventricular pressure and myocardial oxygen efficiency.

The cardiac power, cardiac output and maximum rate of change of left ventricular pressure (LV+dp/dt) together give a sound indication of the systolic function (pump function) of the left ventricle. Cardiac power and cardiac output are influenced by both preload and afterload, whereas LV+dp/dt is affected by preload but relatively independent of afterload. For statistical comparison, a constant preload at a left atrial pressure (LAP) of 15 mmHg was chosen as it represents a considerable challenge to the heart without being greatly unphysiological. Afterload was adjusted in order to maintain aortic pressure at 120/80 mmHg. The perfusion group showed significantly superior cardiac power, cardiac output and LV+dp/dt when compared to the standard preservation group. Moreover, it was observed that hearts preserved in the standard way consistently displayed almost no function and would quickly fail when subjected to even small increases in preload.

The efficiency of the heart can be estimated by dividing the external work by the amount of oxygen consumed. A healthy heart is able to use the energy it forms from aerobic metabolism in an efficient manner to perform work and pump blood through the systemic and pulmonary vasculature. A damaged heart on the other hand contains necrotic myocardium which is unable to produce external work and damaged myocardium which must expend energy on internal work (e.g. repairing cellular damage) rather than external work (e.g. contraction). Perfusion technique hearts showed significantly superior myocardial oxygen efficiency when compared to standard preservation hearts.

Changes in lactate levels give an indication of the underlying state of metabolism of the heart. During periods of hypoxia or anoxia, anaerobic glycolysis leads to the formation of lactate. Conversely, in aerobic conditions lactate is consumed. Both groups showed overall lactate production (and not consumption) following simulated transplant. However, after final assessment, the perfusion technique group had a decreased lactate level compared to the previous measurement, whereas the standard preservation group had an increased lactate level. This is evidence that perfused hearts demonstrated aerobic metabolism unlike the hearts preserved in the standard way which were metabolising anaerobically.

The perfused DCD donor hearts consumed appreciable amounts of oxygen and had decreasing levels of oxygen consumption and lactate production throughout the preservation period. The oxygen consumption of the perfused DCD donor heart was flow-dependent as reflected by a steady increase in oxygen consumption with increasing flows. Oxygen consumption rose in a linear fashion from coronary flows of 10 mL/min up to 40 mL/min. The perfused DCD donor heart consumed more oxygen in the early stages of perfusion (between 0 and 2 hours of perfusion) compared to at a later stage (between 2 and 4 hours). Lactate production also decreased during perfusion.

Perfusate flow was maintained at 20 mL/min during perfusion except during the measurement of myocardial oxygen consumption. This low flow resulted in a perfusion pressure that generally remained between 4-8 mmHg. Although pressure was slightly greater at the end of perfusion compared to the beginning, this increase was not significant.

The superiority of the perfusion method of the invention compared to standard preservation for DCD donor heart storage could be explained by perfusion allowing the heart to metabolise aerobically, which is in contrast to the cold stored heart which cannot. When a donor heart is cold stored, it continues to require energy to maintain cell integrity, and in the absence of oxygen must resort to anaerobic metabolism and suffers the deleterious effects of ischemia. Having already been subject to warm in situ ischemia, cold ischemia during preservation and warm ischemia during implantation, the cold stored DCD donor heart is further damaged upon reperfusion. This series of insults results in a severely compromised myocardium whose recovery is understandably poor.

A perfused DCD donor heart on the other hand is provided during the preservation period with nutrient substrates (glucose, aspartate, adenosine and fructose-1,6-diphosphate) and oxygen allowing it to metabolise aerobically. It receives these via a coronary perfusate which is delivered at a low rate to minimise reperfusion injury. This continuous flow of perfusate also washes out metabolic waste products such as lactate thus better preserving myocardial acid-base balance. The perfusate is fortified with buffers such as TRIS and bicarbonate which provide pH control. Reduced glutathione minimises the oxidative stress caused by blood reperfusion following implantation. In this way, perfusion improves functional and metabolic recovery of the DCD donor heart by preventing the progression of ischemic damage throughout the preservation period and minimising reperfusion injury.

Perfusion preservation resuscitated the DCD donor heart to a degree. Our results showed that during perfusion DCD donor hearts had decreasing oxygen consumption and lactate production. A likely explanation for this is that in the early stages of perfusion, with the ability to metabolise aerobically, the DCD donor heart recovers from the damage sustained during the agonal period. As cell integrity is restored, the heart requires diminishing amounts of oxygen to maintain physiological cell status and also produces less lactate.

Another crucial component of DCD donor heart protection is the cardioplegia used at the commencement of preservation. The standard preservation group received the cardioplegia that is routinely used at the Alfred Hospital in clinical transplantation of the brain dead donor heart. This cardioplegia however was developed to induce cardiac arrest in the routine cardiac surgery and is not be appropriate for the DCD donor heart which is already arrested at the time of cardioplegia administration and has sustained a severe warm ischemic injury. For this reason, we developed a two-part cardioplegia for the perfusion group in order to reduce reperfusion injury. The provision of aspartate, adenosine, cyclosporine and cariporide at the commencement of preservation could add significant benefit to the DCD donor heart. These additives stimulate energy production, decrease coronary resistance, block mitochondrial permeability transition pore (MPTP) formation and reduce the surge of calcium into the intracellular space. In addition, an initial acidic pH further reduces reperfusion injury by preventing MPTP formation and calcium overload. Thus, this two-part cardioplegia affords donor hearts much greater protection against reperfusion injury than standard cardioplegia.

Perfusion pressure is indicative of tissue oedema as pressure rises in the presence of oedema. Perfusion pressure generally remained low in our study and did not increase over time. This suggests that there was little or no oedema formation. The inventors believe that our perfusion technique limited the development of oedema (by using a low flow rate and the oncotic agent sodium lactobionate) and that the presence or absence of oedema did not adversely affect perfused hearts which showed good function.

This study shows that a perfusion method consisting of a two-part cardioplegia and hypothermic perfusion preservation permits the DCD donor heart to recover superior function compared to standard preservation (standard cardioplegia and cold storage). Early recovery does not match the function of a normal (undamaged) heart, but with further recovery over time is sufficient for transplantation. Whilst investigators have previously shown that preservation of the DCD donor heart is possible, many are not clinically applicable due to inappropriate experimental models or the use of ethically unacceptable or prohibitively expensive preservation techniques. The current study has demonstrated the effectiveness of a technique that is relatively simple and cost effective, in an animal model applicable to clinical Maastricht category III DCD donation.

CONCLUSIONS

Our perfusion method (two-part cardioplegia and hypothermic perfusion preservation):
1. Facilitates aerobic metabolism and may promote resuscitation of the DCD donor heart during preservation.
2. Provides superior functional and metabolic recovery of the DCD donor heart compared to standard preservation (standard cardioplegia and cold storage).
3. May allow recovery of the DCD donor heart sufficient for transplantation.
4. Is simple and practical and has the potential for future clinical application.

The invention claimed is:
1. A sterile aqueous solution for gravity microperfusion of donor hearts, the solution consisting of:
    (a) between 10 and 20 mM potassium chloride;
    (b) between 5 and 10 mM magnesium;
    (c) between 0.2 and 1.0 mM calcium;
    (d) between 10 and 40 mM Tris(hydroxymethyl)aminomethane hydrochloride (Tris or THAM), 4-(2-hydroxyethyl)-1-piperazineethanesulfonic acid (HE PES), 3-(Nmorpholino)propanesulfonic acid (MOPS), 2-(N-morpholino)ethanesulfonic acid (MES), N,N-bis-(2-hydroxyethyl)-2-aminoethansulfonic acid (BES), or Ntris(hydroxymethyl)methyl-2-aminoethanesulfonic acid (TES);
    (e) between 10 and 30 mM sodium bicarbonate, for enhancing the out-flow of $CO_2$ from cells;
    (f) between 1 and 40 mM aspartate;
    (g) between 1 and 30 mM glucose;
    (h) between 1 and 20 mM adenosine, cAMP or cGMP;
    (i) between 30 and 100 mM lactobionate;
    (j) between 1 and 20 units/L insulin;
    (k) between 1 and 10 mM fructose diphosphate or a salt thereof;
    (l) between 1 and 10 mM reduced glutathione;
    (m) oxygen saturation using 100% 02; and
    (n) a sufficient concentration of sodium to maintain an ionic strength of sodium in said sterile aqueous solution is to be between 110 and 120 mM.
2. The solution of claim 1 wherein the pH is adjusted to between 7.2 and 7.4, at 22° C., and where said solution has an osmolarity of 300-350 mOsm/L.

* * * * *